United States Patent
Dai et al.

(10) Patent No.: US 10,954,240 B2
(45) Date of Patent: Mar. 23, 2021

(54) COMPOUNDS INHIBITING LEUCINE-RICH REPEAT KINASE ENZYME ACTIVITY

(71) Applicant: Merck Sharp & Dohme Corp., Rahway, NJ (US)

(72) Inventors: Xing Dai, Cranford, NJ (US); Kallol Basu, Hillsborough, NJ (US); Duane DeMong, Hanover, MA (US); Sarah W. Li, Audubon, PA (US); Michael Miller, Scotch Plains, NJ (US); Jack D. Scott, Scotch Plains, NJ (US); Andrew W. Stamford, Chatham, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/507,577

(22) PCT Filed: Aug. 28, 2015

(86) PCT No.: PCT/US2015/047318
§ 371 (c)(1),
(2) Date: Feb. 28, 2017

(87) PCT Pub. No.: WO2016/036586
PCT Pub. Date: Mar. 10, 2016

(65) Prior Publication Data
US 2018/0230152 A1   Aug. 16, 2018

Related U.S. Application Data

(60) Provisional application No. 62/045,184, filed on Sep. 3, 2014.

(51) Int. Cl.
| | | |
|---|---|---|
| C07D 401/14 | (2006.01) | |
| C07D 413/14 | (2006.01) | |
| C07D 487/04 | (2006.01) | |
| C07D 403/14 | (2006.01) | |
| C07D 401/04 | (2006.01) | |
| C07D 403/04 | (2006.01) | |
| A61P 25/16 | (2006.01) | |

(52) U.S. Cl.
CPC ........... *C07D 487/04* (2013.01); *A61P 25/16* (2018.01); *C07D 401/04* (2013.01); *C07D 401/14* (2013.01); *C07D 403/04* (2013.01); *C07D 403/14* (2013.01); *C07D 413/14* (2013.01)

(58) Field of Classification Search
CPC ............................. C07D 413/14; C07D 401/14
USPC ............... 544/124, 364; 546/193, 275.7; 514/232.8, 255, 318, 338, 253.02
See application file for complete search history.

(56) References Cited

U.S. PATENT DOCUMENTS

| | | |
|---|---|---|
| 2008/0146565 A1 | 6/2008 | Dunn et al. |
| 2009/0149468 A1 | 6/2009 | Cao et al. |
| 2010/0317646 A1 | 12/2010 | Mciver et al. |

FOREIGN PATENT DOCUMENTS

| | | |
|---|---|---|
| EP | 2489663 A1 | 8/2012 |
| WO | 2010017046 A1 | 2/2010 |
| WO | 2010083145 A1 | 7/2010 |
| WO | 2012058193 | 5/2012 |
| WO | 2012118679 | 9/2012 |
| WO | 2013124169 A1 | 8/2013 |
| WO | 2014137719 A1 | 9/2014 |
| WO | 2014137723 A1 | 9/2014 |
| WO | 2014137725 A1 | 9/2014 |
| WO | 2014137728 | 9/2014 |
| WO | 2015026683 A1 | 2/2015 |

OTHER PUBLICATIONS

International Search Report for PCT/US2015/047318 dated Dec. 8, 2015, 7 pages.
PubChem-CID-25111112, Create Date: Jan. 12, 2009. 10 pages.
Yamato Suzuki, Jorome Cluzeau, Takafumi Hara, Akira Hirasaw, Gozoh Tsujimoto, Shinya Oishi, Hiroaki Ohno, and Nobutaka Fuji: "Structure-Activity Relationships of Pyrazine-Based CK2 Inhibitors: Synthesis and Evaluation of 2,6-Disubstitued Pyrazines and 4,6-Disubstituted Pyrimidines", vol. 341, Feb. 26, 2008 (Feb. 26, 2008), pp. 554-561.

*Primary Examiner* — Patricia L Morris
(74) *Attorney, Agent, or Firm* — Sylvia A. Ayler; Catherine D. Fitch

(57) ABSTRACT

The present invention is directed to substituted certain reversed indazole compounds of Formula (I): and pharmaceutically acceptable salts thereof, wherein R1, R2, R3, R4, R9, and A are as defined herein, which are potent inhibitors of LRRK2 kinase and useful in the treatment or prevention of diseases in which the LRRK2 kinase is involved, such as Parkinson's Disease. The invention is also directed to pharmaceutical compositions comprising these compounds and the use of these compounds and compositions in the prevention or treatment of such diseases in which LRRK-2 kinase is involved.

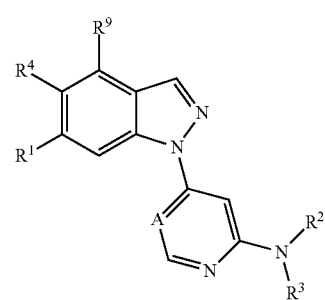

5 Claims, No Drawings

COMPOUNDS INHIBITING LEUCINE-RICH REPEAT KINASE ENZYME ACTIVITY

BACKGROUND OF THE INVENTION

Parkinson's disease (PD) is a common neurodegenerative disease caused by progressive loss of mid-brain dopaminergic neurons leading to abnormal motor symptoms such as bradykinesia, rigidity and resting tremor. Many PD patients also experience a variety of non-motor symptoms including cognitive dysfunction, autonomic dysfunction, emotional changes and sleep disruption. The combined motor and non-motor symptoms of Parkinson's disease severely impact patient quality of life.

While the majority of PD cases are idiopathic, there are several genetic determinants such as mutations in SNCA, Parkin, PINK1, DJ-1 and LRRK2. Linkage analysis studies have demonstrated that multiple missense mutations in the Leucine-Rich Repeat Kinase 2 (LRRK2) gene lead to an autosomal late onset form of PD. LRRK2 is a 286 kDa cytoplasmic protein containing kinase and GTPase domains as well as multiple protein-protein interaction domains. See for example, Aasly et al., Annals of Neurology, Vol. 57(5), May 2005, pp. 762-765; Adams et al., Brain, Vol. 128, 2005, pp. 2777-85; Gilks et al., Lancet, Vol. 365, Jan. 29, 2005, pp. 415-416, Nichols et al., Lancet, Vol. 365, Jan. 29, 2005, pp. 410-412, and U. Kumari and E. Tan, FEBS journal 276 (2009) pp. 6455-6463.

In vitro biochemical studies have demonstrated that LRRK2 proteins harboring the PD associated proteins generally confer increased kinase activity and decreased GTP hydrolysis compared to the wild type protein (Guo et al., Experimental Cell Research, Vol, 313, 2007, pp. 3658-3670) thereby suggesting that small molecule LRRK2 kinase inhibitors may be able to block aberrant LRRK2-dependent signaling in PD. In support of this notion, it has been reported that inhibitors of LRRK2 are protective in models of PD (Lee et al., Nature Medicine, Vol 16, 2010, pp. 998-1000).

LRRK2 protein has also been demonstrated to be associated with Lewy bodies, a pathological hallmark of PD as well as other neurodegenerative diseases such as Lewy body dementia (Zhu et al., Molecular Neurodegeneration, Vol 30, 2006, pp. 1-17) thereby suggesting that LRRK2 may be associated with the pathogenesis of these diseases.

A growing body of evidence also suggests a role for LRRK2 in immune cell function in the brain with LRRK2 inhibition demonstrated to attenuate microglial inflammatory responses (Moehle et al., The Journal of Neuroscience Vol 32, 2012, pp. 1602-1611). Neuroinflammation is a hallmark of a number of neurodegenerative diseases such as PD and Alzheimer's disease, thereby suggesting that LRRK2 inhibitors may have utility in the treatment of neuroinflammation in these disorders.

Genome-wide association studies also highlight LRRK2 in the modification of susceptibility to the chronic autoimmune Crohn's disease and leprosy (Zhang et al., The New England Jopuranl of Medicine, Vol 361, 2009, pp. 2609-2618; Umeno et al., Inflammatory Bowel Disease Vol 17, 2011, pp. 2407-2415). LRRK2 is also associated with certain types of cancer, e.g. melanoma as well as renal and thyroid carcinomas (Saunders-Pullman et al., Movement Disorders, Vol 25, 2010, pp. 2536-2541; Looyenga, et al., Proceedings of the National Academy of Sciences, USA, Vol 108, 2011, pp. 1439-1444).

Accordingly, compounds and compositions effective at inhibiting LRRK2 activity may provide a treatment for neurodegenerative diseases such as Parkinson's disease, Lewy body dementia, neuroinflammation, and for diseases such as Crohn's disease, leprosy and cancer.

SUMMARY OF THE INVENTION

The present invention is directed to certain substituted indazole compounds, which are collectively or individually referred to herein as "compound(s) of the invention" or "compounds of Formula (I)", as described herein. The compounds of the invention are potent inhibitors of LRRK2 kinase and may be useful in the treatment or prevention of diseases in which the LRRK2 kinase is involved, such as Parkinson's Disease. The invention is also directed to pharmaceutical compositions comprising a compound of the invention and the use of these compounds and compositions in the prevention or treatment of such diseases in which LRRK-2 kinase is involved.

DETAILED DESCRIPTION OF THE INVENTION

For each of the following embodiments, any variable not explicitly defined in the embodiment is as defined in Formula (I) or (IA). In each of the embodiments described herein, each variable is selected independently of the other unless otherwise noted.

In one embodiment, the compounds of the invention have the structural Formula (I):

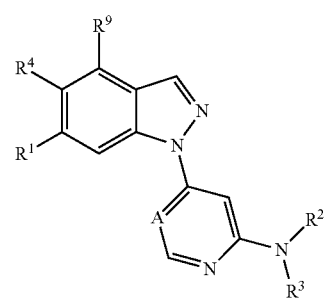

or a pharmaceutically acceptable salt thereof,
wherein $R^1$ is selected from the group consisting of:
 a) hydrogen,
 b) halo,
 c) cyano,
 d) hydroxyl,
 e) $C_{2-6}$ alkenyl, which is optionally substituted with one to three substitutents independently selected from the group consisting of halo, cyano and $R^5$;
 $OC_{2-6}$ alkenyl, which is optionally substituted with one to three substitutents independently selected from the group consisting of halo, cyano and $R^5$;
 g) $R^5$,
 h) $OR^5$,
 i) $R^7$,
 j) $S(O)_m R^5$,
 k) $S(O)_m R^7$,
 l) $(C=O)R^7$,
 m) $(C=O)R^5$, n) (C=O)OR$^5$,
o) NR$^c$R$^d$, and
p)

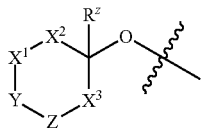

X$^1$, X$^2$ and X$^3$ are each independently selected from the group consisting of a bond or CR$^e$R$^f$;
Y is O, CR$^a$R$^b$ or NR$^c$;
Z is O, CR$^a$R$^b$ or NR$^c$;
R$^z$ is selected from the group consisting of hydrogen and C$_{1-3}$ alkyl, which is optionally substituted with one to three substituents independently selected from the group consisting of halo, hydroxyl, cyano, NH(C$_{1-3}$ alkyl), N(C$_{1-3}$ alkyl)$_2$, OC$_{1-6}$ alkyl, and C$_{3-8}$ cycloalkyl;
A is CH or N;
R$^2$ is selected from the group consisting of hydrogen and C$_{1-6}$ alkyl, which is optionally substituted with one to three substitutents independently selected from the group consisting of:
  a) halo,
  b) cyano,
  c) R$^5$,
  d) R$^7$,
  e) OR$^5$, and
  f) NR$^c$R$^d$;
R$^3$ is selected from the group consisting of:
  a) hydrogen,
  b) C$_{1-6}$ alkyl, which is optionally substituted with one to three substitutents independently selected from the group consisting of halo, cyano, OR$^5$ and NR$^c$R$^d$,
  c) C$_{3-8}$ cycloalkyl, which is optionally substituted with one to three substitutents independently selected from the group consisting of halo, cyano, OR$^5$ and NR$^c$R$^d$,
  d) heterocyclyl, which is optionally substituted with one to three substitutents independently selected from the group consisting of halo, cyano, oxo, R$^5$, OR$^5$ and NR$^c$R$^d$,
  e) heteroaryl, which is optionally substituted with one to three substitutents independently selected from the group consisting of halo, cyano, oxo, R$^5$, OR$^5$ and NR$^c$R$^d$;
  f) C$_{4-8}$ cycloalkenyl, which is optionally substituted with one to three substitutents independently selected from the group consisting of halo, cyano, OR$^5$ and NR$^c$R$^d$,
  g) (C=O)R$^7$,
  h) (C=O)R$^5$,
  i) S(O)$_m$R$^5$, and
  j) S(O)$_m$R$^7$;
or R$^2$ and R$^3$ can be taken together with the atoms to which they are attached to form a 3 to 8 membered heterocyclic or heteroaryl ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
  a) halo,
  b) oxo,
  c) cyano,
  d) OR$^5$,
  e) NR$^c$R$^d$,
  f) SO$_3$H,
  g) S(O)$_m$R$^5$,
  h) S(O)$_m$R$^7$,
  i) R$^5$,
  j) R$^6$,
  k) R$^7$,
  l) (C=O)R$^5$,
  m) (C=O)OR$^5$,
  n) (C=O)R$^7$, and
  o) (C=O)NR$^c$R$^d$;
R$^4$ is selected from the group consisting of: hydrogen, halo, cyano, OR$^5$, aryl, heteroaryl, C$_{3-8}$ cycloalkyl, C$_{4-8}$ cycloalkenyl, C$_{4-8}$ heterocyclyl and C$_{1-6}$ alkyl, which is optionally substituted with one to three substituents independently selected from the group consisting of halo, cyano, OC$_{1-3}$ alkyl, NR$^c$R$^d$ and hydroxy;
R$^5$ is selected from the group consisting of hydrogen or C$_{1-6}$ alkyl, which is optionally substituted with one to three substituents independently selected from the group consisting of:
  a) halo,
  b) hydroxyl,
  c) OC$_{1-6}$ alkyl,
  d) NR$^c$R$^d$,
  e) (C=O)NR$^c$R$^d$,
  f) S(O)$_m$R$^8$,
  g) S(O)$_m$R$^7$,
  h) R$^7$, and
  i) OR$^7$;
R$^6$ is C$_{1-6}$ alkyl, which is optionally substituted with one to three substituents independently selected from the group consisting of halo and hydroxyl;
or R$^5$ and R$^6$ can be taken together with the atoms to which they are attached to form a 4 to 8 membered heterocyclic, 3 to 8 membered carbocyclic, aryl or heteroaryl ring, wherein said heterocyclic and heteroaryl rings may contain from one to three heteroatoms selected from N, O and S, wherein said heterocyclic, carbocyclic, aryl and heteroaryl rings are optionally substituted with one to three substituents independently selected from the group consisting of:
  a) halo,
  b) oxo,
  c) cyano,
  d) hydroxyl,
  e) C$_{1-3}$ alkyl, which is optionally substituted with one to three halo,
  f) C$_{3-8}$ cycloalkyl,
  g) OC$_{1-3}$ alkyl, which is optionally substituted with one to three halo, and
  h) OC$_{3-8}$ cycloalkyl;
R$^7$ is selected from the group consisting of C$_{4-8}$ heterocyclyl, C$_{3-8}$ cycloalkyl, C$_{4-8}$ cycloalkenyl, aryl or heteroaryl, wherein said heterocyclyl, cycloalkyl, cycloalkenyl, aryl and heteroaryl groups are optionally substituted with one to three substituents independently selected from the group consisting of:
  a) halo,
  b) cyano,
  c) hydroxyl,
  d) oxo,
  e) C$_{1-3}$ alkyl, which is optionally substituted with one to four substituents independently selected from the group consisting of hydroxyl, halo, cyano, heterocyclyl, OC$_{1-3}$ alkyl and NR$^c$R$^d$,
  f) OC$_{1-3}$ alkyl, which is optionally substituted with one to four substituents independently selected from the group consisting of hydroxyl, halo, cyano, heterocyclyl, OC$_{1-3}$ alkyl, NR$^c$R$^d$, aryl and heteroaryl, g) $C_{3-8}$ cycloalkyl, which is optionally substituted with one to four substituents independently selected from the group consisting of hydroxyl, halo, cyano, heterocyclyl, $OC_{1-3}$ alkyl and $NR^cR^d$, h) aryl, which is optionally substituted with one to four substituents independently selected from the group consisting of hydroxyl, halo, cyano, heterocyclyl, $OC_{1-3}$ alkyl, $S(O)_mNR^cR^d$, $C(O)NR^cR^d$ and $NR^cR^d$, i) heteroaryl, which is optionally substituted with one to four substituents independently selected from the group consisting of hydroxyl, halo, cyano, heterocyclyl, $OC_{1-3}$ alkyl, $S(O)_mNR^cR^d$, $C(O)NR^cR^d$ and $NR^cR^d$, j) heterocyclyl, which is optionally substituted with one to four substituents independently selected from the group consisting of hydroxyl, halo, cyano, $OC_{1-3}$ alkyl and $NR^cR^d$, k) $C_{4-8}$ cycloalkenyl, which is optionally substituted with one to four substituents independently selected from the group consisting of hydroxyl, halo, cyano, heterocyclyl, $OC_{1-3}$ alkyl and $NR^cR^d$;

$R^8$ is hydrogen or $C_{1-6}$ alkyl, which is optionally substituted with one to three substituents independently selected from the group consisting of:
  a) halo,
  b) cyano,
  c) hydroxyl,
  d) $OC_{1-3}$ alkyl, which is optionally substituted with one to four substituents independently selected from the group consisting of hydroxyl, halo and $NR^eR^f$, and
  e) $C_{3-8}$ cycloalkyl;

$R^9$ is selected from the group consisting of:
  a) $C_{1-3}$ alkyl, which is optionally substituted with one to three substituents independently selected from the group consisting of halo,
  b) halo,
  c) cyano,
  d) hydroxyl, and
  e) $OC_{1-3}$ alkyl, which is optionally substituted with one to three substituents independently selected from the group consisting of halo;

$R^a$ is selected from the group consisting of hydrogen and $C_{1-6}$ alkyl;

$R^b$ is selected from the group consisting of hydrogen and $C_{1-6}$ alkyl;

$R^c$ is selected from the group consisting of:
  a) hydrogen,
  b) $C_{1-3}$ alkyl, which is optionally substituted with one to three substituents independently selected from the group consisting of halo, hydroxyl, cyano, heteroaryl, aryl, $NH(C_{1-3}$ alkyl), $N(C_{1-3}$ alkyl$)_2$, $OC_{1-6}$ alkyl, and $C_{3-8}$ cycloalkyl;

$R^d$ is selected from the group consisting of:
  a) hydrogen,
  b) $C_{3-8}$ cycloalkyl,
  c) $C_{3-6}$ heterocyclyl,
  d) $C_{1-3}$ alkyl,
  e) (C=O)$C_{1-3}$ alkyl,
  f) aryl, and
  g) heteroaryl;

wherein said cycloalkyl, heterocyclyl, alkyl, aryl and heteroaryl groups are each optionally substituted with one to three substituents independently selected from the group consisting of halo, hydroxyl, cyano, $R^8$, $SO_2R^8$, $OC_{1-6}$ alkyl and $C_{3-8}$ cycloalkyl;

or $R^c$ and $R^d$ can be taken together with the atoms to which they are attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of halo, cyano, hydroxyl, $C_{1-3}$ alkyl and $OC_{1-3}$ alkyl;

$R^e$ is selected from the group consisting of hydrogen and $C_{1-3}$ alkyl;

$R^f$ is selected from the group consisting of hydrogen and $C_{1-3}$ alkyl; and m is an integer from zero to two.

In one embodiment, in Formula (I), $R^4$ is H.

In one embodiment, in Formula (I), $R^9$ is selected from the group consisting of H and halo.

In one embodiment, in Formula (I), $R^4$ is H and $R^9$ is selected from the group consisting of H and halo.

In one embodiment, in Formula (I), A is CH.

In one embodiment, in Formula (I), A is N.

In one embodiment, in Formula (I):
  $R^4$ is H;
  $R^9$ is selected from the group consisting of H and halo; and
  A is CH.

In one embodiment, in Formula (I):
  $R^4$ is H;
  $R^9$ is selected from the group consisting of H and halo; and
  A is N.

The following alternative embodiments of $R^1$ are contemplated in combination with any of the embodiments described hereinabove.

In one embodiment, in Formula (I), $R^1$ is selected from the group consisting of H, —(C$_{1-6}$)alkyl, —(C$_{1-6}$)alkenyl, —O(C$_{1-6}$)alkyl, heteroaryl, —(C$_{3-6}$)cycloalkyl, and —(C$_{3-6}$)cycloalkenyl, wherein each said heteroaryl, —(C$_{3-6}$)cycloalkyl, and —(C$_{3-6}$)cycloalkenyl, is optionally substitutent with from 1 to 3 substituents independently selected from the group consisting of alkyl, alkoxy, halo, cyano, hydroxyl, and oxo.

In one embodiment, in Formula (I), $R^1$ is selected from the group consisting of H, —(C$_{1-6}$)alkyl, —(C$_{1-6}$)alkenyl, —O(C$_{1-6}$)alkyl, pyrazolyl, pyridinyl, cyclopropyl, cyclobutyl, cyclopentyl, cyclohexyl, and —(C$_{4-6}$)cycloalkenyl, wherein each said pyrazolyl, pyridinyl, cyclopropyl, cyclobutyl, cyclopentyl, cyclohexyl, and —(C$_{4-6}$)cycloalkenyl, is optionally substitutent with from 1 to 3 substituents independently selected from the group consisting of alkyl, alkoxy, halo, cyano, hydroxyl, and oxo.

The following alternative embodiments of $R^2$ and $R^3$ are contemplated in combination with any of the embodiments described hereinabove.

In one embodiment, in Formula (I), $R^2$ and $R^3$ are taken together with the atoms to which they are shown attached to form a 3 to 8 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:
  a) halo,
  b) oxo,
  c) cyano,
  d) $OR^5$,
  e) $NR^cR^d$,
  f) $SO_3H$
  g) $S(O)_mR^5$,
  h) $S(O)_mR^7$,
  i) $R^5$,
  j) $R^6$, k) $R^7$,
l) $(C=O)R^5$,
m) $(C=O)OR^5$,
n) $(C=O)R^7$ and
o) $(C=O)NR^cR^d$.

In another embodiment, in Formula (I), $R^2$ and $R^3$ are taken together with the atoms to which they are attached to form a 6 membered heterocyclic ring, wherein said ring may contain from one to three heteroatoms selected from N, O and S, wherein the sulfur is optionally oxidized to the sulfone or sulfoxide, and which ring is optionally substituted with one to four substituents each independently selected from the group consisting of:

a) halo,
b) oxo,
c) $OR^5$,
d) $NR^cR^d$,
e) $S(O)_mR^5$,
f) $S(O)_mR^7$,
f) $R^5$,
g) $R^6$,
h) $R^7$,
i) $(C=O)R^5$,
j) $(C=O)OR^5$ and
k) $(C=O)R^7$.

In another embodiment, in Formula (I), $R^2$ and $R^3$ are taken together with the atoms to which they are shown attached to form a morpholinyl group, a piperazinyl group, a piperazinyl group, a piperadinyl group, a 5,6,7,8-tetrahydroimidazo[1,2-a]pyrazinyl, a 5,6,7,8-tetrahydro-[1,2,4]triazolo[4,3-a]pyrazinyl, an azetidinyl group, or a pyrrolidinyl group, wherein each said group is optionally substituted with from 1 to 4 substituents selected from the group consisting of:

a) halo,
b) oxo,
c) $OR^5$,
d) $NR^cR^d$,
e) $S(O)_mR^5$,
f) $S(O)_mR^7$,
f) $R^5$,
g) $R^6$,
h) $R^7$,
i) $(C=O)R^5$,
j) $(C=O)OR^5$ and
k) $(C=O)R^7$.

In another embodiment, in Formula (I), $R^2$ and $R^3$ are taken together with the atoms to which they are shown attached to form a morpholinyl group, a piperazinyl group, a piperazinyl group, a piperadinyl group, a 5,6,7,8-tetrahydroimidazo[1,2-a]pyrazinyl, a 5,6,7,8-tetrahydro-[1,2,4]triazolo[4,3-a]pyrazinyl, an azetidinyl group, or a pyrrolidinyl group, wherein each said group is optionally substituted with from 1 to 4 substituents selected from the group consisting of: —$SO_2CH_3$, oxo, hydroxyl, —$(C_{1-3})$alkyl, —O—$(C_{1-3})$alkyl, —$(C_{1-3})$alkyl-OH, halo, $(C=O)O(C_{1-3})$alkyl, —$(C=O)NH(C_{1-3})$alkyl, —$(C=O)N((C_{1-3})$alkyl$)_2$, and —$(C_{0-3})$alkyl-$(C_{3-6})$cycloalkyl.

In another embodiment, the compounds of the invention include those identified herein as Examples in the tables below, and pharmaceutically acceptable salts thereof.

Another embodiment provides a pharmaceutical composition comprising an inert carrier and a compound of the invention, or a pharmaceutically acceptable salt thereof.

Another embodiment provides a method of treating Parkinson's Disease in a mammalian patient in need of such treatment, which comprises administering to the patient a therapeutically effective amount of a compound of the invention, or a pharmaceutically acceptable salt thereof.

Another embodiment provides the use of a compound of the invention, or a pharmaceutically acceptable salt thereof, and a pharmaceutically acceptable carrier, for the manufacture of a medicament for the treatment of Parkinson's Disease. The invention may also encompass the use of a compound of the invention, or a pharmaceutically acceptable salt thereof, and a pharmaceutically acceptable carrier, in therapy.

Another embodiment provides for medicaments or pharmaceutical compositions which may be useful for treating diseases or disorders in which LRRK2 is involved, such as Parkinson's Disease, which comprise a compound of the invention, or a pharmaceutically acceptable salt thereof, and a pharmaceutically acceptable carrier.

Another embodiment provides for the use of a compound of the invention which may be useful for treating diseases or disorders in which LRRK2 is involved, such as Parkinson's Disease.

Another embodiment provides a method for the manufacture of a medicament or a composition which may be useful for treating diseases or disorders in which LRRK2 is involved, such as Parkinson's Disease, comprising combining a compound of the invention with one or more pharmaceutically acceptable carriers.

The compounds of the invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Unless a specific stereochemistry is indicated, the present invention is meant to comprehend all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Tautomers of compounds defined in Formula I are also included within the scope of the present invention. For example, compounds including carbonyl —CH$_2$C(O)— groups (keto forms) may undergo tautomerism to form hydroxyl —CH=C(OH)— groups (enol forms). Both keto and enol forms are included within the scope of the present invention.

When any variable (e.g. $R^5$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be understood as meaning that the group in question is either unsubstituted or may be substituted with one or more substituents.

As used herein, "alkyl" is intended to mean linear or branched structures having no carbon-to-carbon double or triple bonds. Thus, $C_{1-4}$ alkyl is defined to identify the group as having 1, 2, 3 or 4 carbons in a linear or branched arrangement, such that $C_{1-4}$ alkyl specifically includes, but is not limited to, methyl, ethyl, n-propyl, iso-propyl, n-butyl, iso-butyl and tert-butyl.

As appreciated by those of skill in the art, "halo" or "halogen" as used herein is intended to include chloro (Cl), fluoro (F), bromo (Br) and iodo (I).

The term "cycloalkyl" shall mean cyclic rings of alkanes of three to eight total carbon atoms, unless otherwise indicated, or any number within this range (i.e., cyclopropyl, cyclobutyl, cyclopentyl, cyclohexyl, cycloheptyl, methylcyclopropyl, 2,2-dimethyl-cyclobutyl, 2-ethyl-cyclopentyl or cyclooctyl) and also includes bicyclic or fused spirocyclic compounds.

The term "cycloalkenyl" shall mean cyclic rings of four to eight total carbon atoms, unless otherwise indicated, or any number within this range where one or two degrees of unsaturation are present. Non-limiting examples of said cycloalkenyl groups are: cyclohexenyl, cyclopentenyl, cyclooctadienyl.

If no number of carbon atoms is specified, the term "alkenyl" refers to a non-aromatic hydrocarbon radical, straight or branched, containing from 2 to 10 carbon atoms and at least 1 carbon to carbon double bond. Preferably 1 carbon to carbon double bond is present, and up to 4 non-aromatic carbon-carbon double bonds may be present. Thus, "C2-C6 alkenyl" means an alkenyl radical having from 2 to 6 carbon atoms. Alkenyl groups include ethenyl, propenyl, butenyl and hexenyl. As described above with respect to alkyl, the straight or branched portion of the alkenyl group may contain double bonds and may be substituted if a substituted alkenyl group is indicated.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

The term "heteroaryl", as used herein, represents a stable monocyclic, bicyclic or tricyclic ring of up to 10 atoms in each ring, wherein at least one ring is aromatic and contains from 1 to 4 heteroatoms selected from the group consisting of O, N and S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, and tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "heterocycle" or "heterocyclyl" as used herein is intended to mean a 5- to 10-membered nonaromatic ring, unless otherwise specified, containing from 1 to 4 heteroatoms selected from the group consisting of O, N, S, SO, or $SO_2$ and includes bicyclic groups. The heterocyclyl group also includes rings that possess one or two degrees of unsaturation. "Heterocyclyl" therefore includes, but is not limited to the following: piperazinyl, piperidinyl, pyrrolidinyl, morpholinyl, thiomorpholinyl, tetrahydropyranyl, dihydropiperidinyl, tetrahydrothiophenyl, azetidinyl and the like. If the heterocycle contains a nitrogen, it is understood that the corresponding N-oxides thereof are also emcompassed by this definition.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Salts in the solid form may exist in more than one crystal structure, and may also be in the form of hydrates. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Salts derived from inorganic bases include aluminum, ammonium, calcium, copper, ferric, ferrous, lithium, magnesium, manganic salts, manganous, potassium, sodium, zinc, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. Similarly, the salts of the acidic compounds are formed by reactions with the appropriate inorganic or organic base. It will be understood that, as used herein, references to the compounds of Formula I are meant to also include the pharmaceutically acceptable salts.

Exemplifying the invention is the use of the compounds disclosed in the Examples and herein. Specific compounds within the present invention include a compound which may be selected from the group consisting of the compounds disclosed in the following Examples and pharmaceutically acceptable salts thereof and individual diastereomers thereof.

The subject compounds are useful in a method of inhibition of LRRK2 receptors in a patient such as a mammal in need of such antagonism comprising the administration of an effective amount of the compound. The present invention is directed to the use of the compounds disclosed herein as inhibitors of LRRK2 receptors. In addition to primates, especially humans, a variety of other mammals can be treated according to the method of the present invention.

Another embodiment of the present invention is directed to a method for the treatment, control, amelioration, or reduction of risk of a disease or disorder in which the LRRK2 kinase is involved in a patient that comprises administering to the patient a therapeutically effective amount of a compound that is an inhibitor of LRRK2 kinase.

The present invention is further directed to a method for the manufacture of a medicament for inhibition of LRRK2 receptors activity in humans and animals comprising combining a compound of the present invention with a pharmaceutical carrier or diluent.

The subject treated in the present methods is generally a mammal, for example a human being, male or female, in whom inhibition of LRRK2 kinase activity is desired. The term "therapeutically effective amount" means the amount of the subject compound that will elicit the biological or medical response of a tissue, system, animal or human that is being sought by the researcher, veterinarian, medical doctor or other clinician.

The terms "treating" or "treatment" of a disease as used herein includes: inhibiting the disease, i.e., arresting or reducing the development of the disease or its clinical symptoms; or relieving the disease, i.e., causing regression of the disease or its clinical symptoms. The term "preventing" or "prevention" of a disease as used herein includes: causing the clinical symptoms of the disease not to develop in a mammal that may be exposed to or predisposed to the disease but does not yet experience or display symptoms of the disease, and the like.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The ability of the compounds of the present invention to act as LRRK2 kinase inhibitors may make them useful pharmacological agents for disorders that involve LRRK2 kinase in humans and animals, but particularly in humans.

In another embodiment the invention provides a method of inhibiting LRRK2 Kinase activity (this is to say, inhibiting the kinase activity associated with Leucine-Rich Repeat Kinase 2 [LRRK2], a multidomain protein containing kinase and GTPase enzymatic activities) in a patient in need of therapy for a condition amenable to treatment by such kinase activity inhibition, for example, treatment or prevention of neurologic damage associated with Parkinson's disease, for example, improvement in dopaminergic tone and in providing symptomatic benefit, for example, in treating, alleviating, ameliorating, or managing motor and non-motor symptoms of Parkinson's disease, and other conditions that may be treated or prevented by inhibition of LRRK2 kinase. Of particular importance is the acute or prophylactic treatment of Parkinson's Disease.

The subject compounds may be further useful in a method for the prevention, treatment, control, amelioration, or reduction of risk of the diseases, disorders and conditions noted herein.

The subject compounds may be further useful in a method for the prevention, treatment, control, amelioration, or reduction of risk of the aforementioned diseases, disorders and conditions in combination with other agents.

The compounds of the present invention may be used in combination with one or more other drugs in the treatment, prevention, control, amelioration, or reduction of risk of diseases or conditions for which compounds of Formula I or the other drugs may have utility, where the combination of the drugs together are safer or more effective than either drug alone. Such other drug(s) may be administered, by a route and in an amount commonly used therefore, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with one or more additional therapeutic agents, for example: L-DOPA; dopaminergic agonists such as quinpirole, ropinirole, pramipexole, pergolide and bromocriptine; MAO-B inhibitors such as rasagiline, deprenyl and selegiline; DOPA decarboxylase inhibitors such as carbidopa and benserazide; and COMT inhibitors such as tolcapone and entacapone; or potential therapies such as an adenosine A2a antagonists, metabotropic glutamate receptor 4 modulators, or growth factors such as brain derived neurotrophic factor (BDNF), and a pharmaceutically acceptable carrier.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, buccal or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl mono stearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require inhibition of LRRK2 kinase activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may be provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Methods for preparing the compounds of this invention are illustrated in the following Schemes and Examples. Starting materials are made according to procedures known in the art or as illustrated herein.

PREPARATIVE EXAMPLES

The compounds of the present invention can be prepared readily according to the following Schemes and specific examples, or modifications thereof, using readily available starting materials, reagents and conventional synthesis procedures. In these reactions, it is also possible to make use of variants which are themselves known to those of ordinary skill in this art but are not mentioned in greater detail. The general procedures for making the compounds claimed in this invention can be readily understood and appreciated by one skilled in the art from viewing the following Schemes.

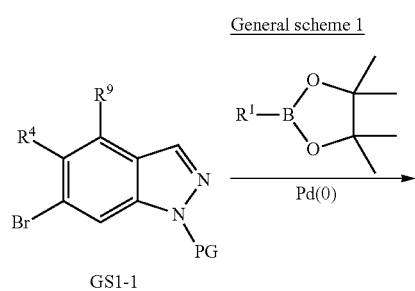

General scheme 1

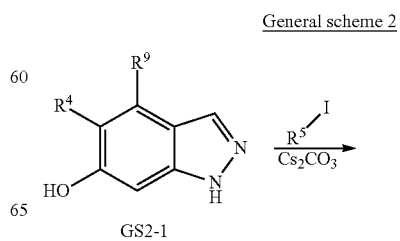

Treatment of a suitable bromo-indazole GS1-1 under palladium catalyzed cross coupling conditions with a boronic acid and the like will afford GS1-2 (General scheme 1). Removal of the protecting group under standard conditions can provide compounds GS1-3. Compounds GS1-3 can then undergo copper-catalyzed cross coupling with the requisite boronic acid to afford GS1-4. Palladium mediated amination with the appropriate amines will provide examples GS1-5.

General scheme 2

-continued

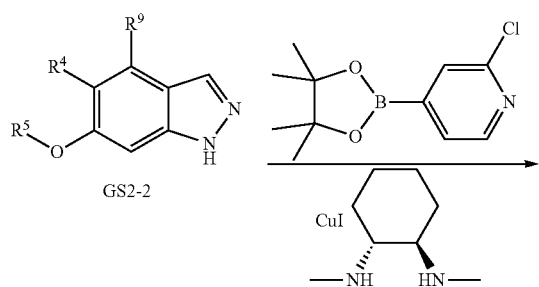

GS2-2

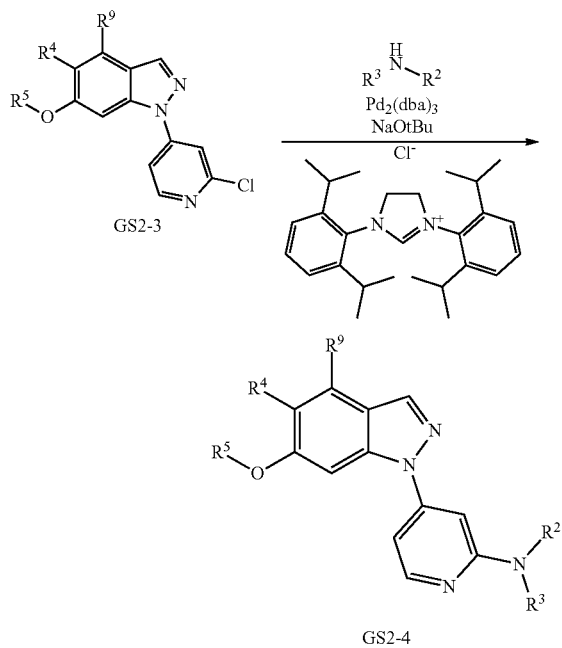

GS2-3

GS2-4

Alternatively, when R5 is a suitable substituted or unsubstituted alkyl group, a hydroxyindazole such as GS2-1 can be converted to the alkoxyindazole GS2-2 by alkylation (General scheme 2). Compounds GS2-2 can then undergo copper-catalyzed cross coupling with the requisite boronic acid to afford GS2-3. Palladium mediated amination with the appropriate amines will provide examples GS2-4.

General Scheme 3

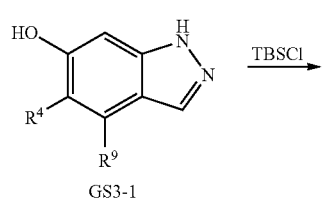

GS3-1

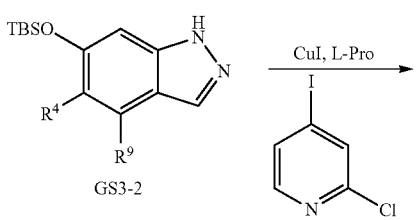

GS3-2

-continued

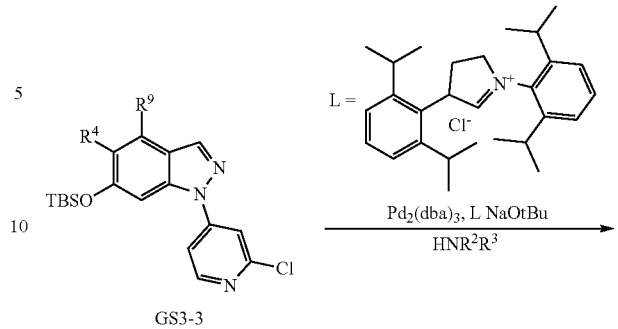

GS3-3

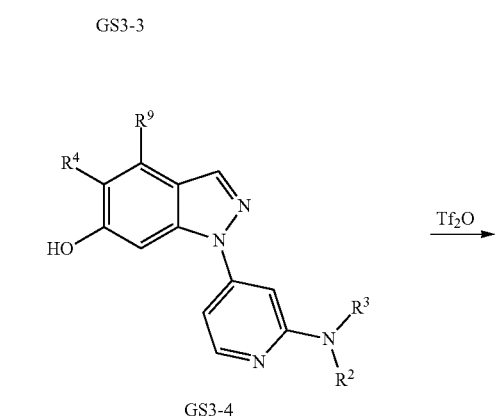

GS3-4

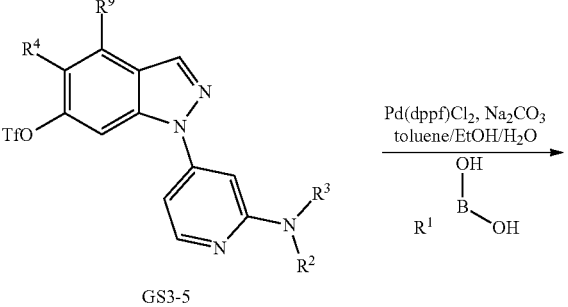

GS3-5

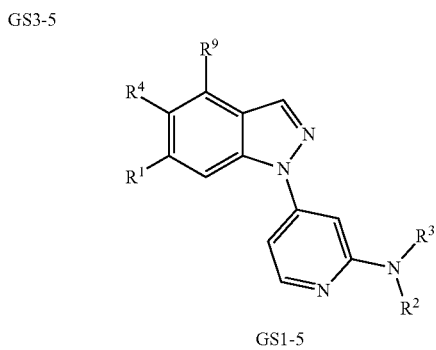

GS1-5

General scheme 3 describes an alternative method for the preparation of examples GS1-5. A hydroxy indazole GS3-1 can be treated with TBS-Cl and a suitable base to afford GS3-2. Copper-catalyzed N-arylation of GS3-2 will afford intermediates GS3-3. Palladium-mediated amination of GS3-3 with amines $HNR^2R^3$ will afford intermediates GS3-4. Conversion of the hydroxyl in present in intermediates GS3-4 to the triflate GS3-5 and the like can then be followed by palladium-mediated cross coupling with a suitable $R^1$—$B(OH)_2$ or boronate ester to afford examples GS1-5.

General Scheme 4

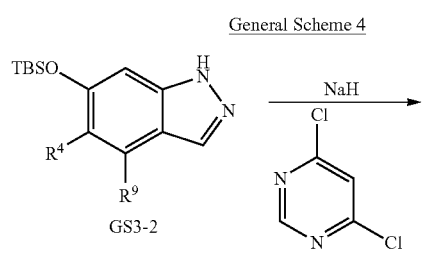

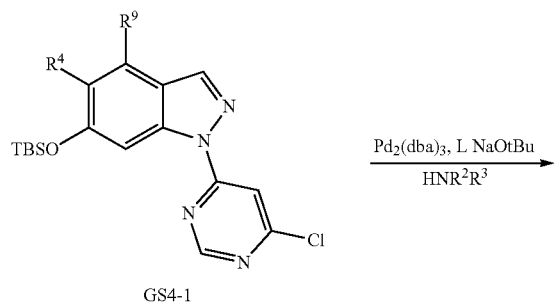

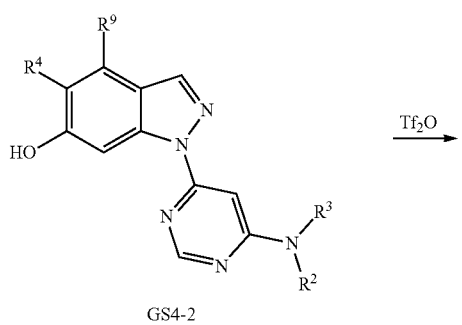

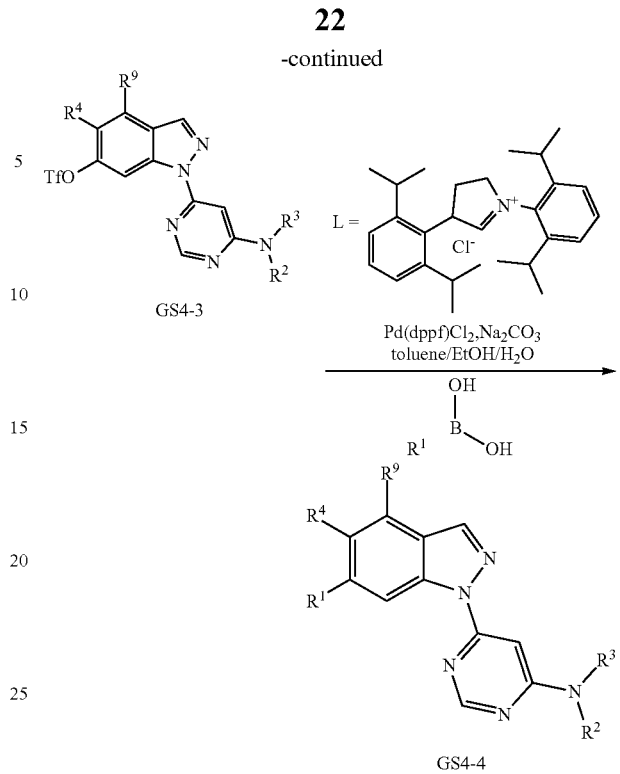

General Scheme 4 provides a method for preparing examples GS4-4. Intermediates GS3-2 can be treated with sodium hydride, followed by 4,6-dichloropyrimidine to afford intermediates GS4-1. Palladium-mediated amination of GS4-1 with amines $HNR^2R^3$ can afford intermediates GS4-2. Conversion of the hydroxyl present in GS4-2 to the triflate GS4-3 and the like can be followed by palladium-mediated cross coupling with boronic acids $R^1$—$B(OH)_2$ or a corresponding boronate ester to afford examples GS4-4.

Experimentals

Abbreviations used in the experimentals may include, but are not limited to the following:

| | | | |
|---|---|---|---|
| ACN | Acetonitrile | AcOH | Acetic acid |
| Aq | Aqueous | Bn | Benzyl |
| BOC | tert-Butoxycarbonyl | BOC$_2$O Boc$_2$O | BOC Anhydride |
| Bu | Butyl | C (or ° C.) | degrees Celsius |
| Cbz | benzyloxycarbonyl | DBU | 1,8-Diazabicyclo[5.4.0]undec-7-ene |
| DCM | Dichloromethane | DIPEA | Diisopropylethylamine |
| DEAD | diethylazodicarboxylate | DIAD | diisopropylazodicarboxylate |
| DMA | N,N-Dimethylacetamide | DMAP | 4-Dimethylaminopyridine |
| DME | 1,2-dimethoxyethane | DMF | Dimethylformamide |
| DMSO | Dimethyl sulfoxide | dppf | 1,1'-(bis-diphenylphosphino)ferrocene |
| EDCI | 1-(3-Dimethylaminopropyl)-3-ethylcarbodiimide hydrochloride | EDC | 1-(3-Dimethylaminopropyl)-3-ethylcarbodiimide hydrochloride |
| EI | Electron ionization | Eq | Equivalents |
| Et | Ethyl | EtOAc | Ethyl acetate |
| EtOH | Ethanol | g | grams |
| h, hr | hours | $^1$H | proton |
| HATU | N,N,N',N'-Tetramethyl-O-(7-Azabenzotriazol-1-yl)uronium hexafluorophosphate | Hex | hexanes |
| HOBT | 1-Hydroxybenzotriazole | HOBT•H$_2$O | 1-Hydroxybenzotriazole hydrate |
| HOTS | para-toluene sulfonic acid (see also TsOH) | HOTS•H$_2$O | para-toluene sulfonic acid hydrate (see also TsOH•H$_2$O) |

| | | | |
|---|---|---|---|
| HMPA | hexamethylphosphoramide | HPLC | High pressure liquid chromatography |
| IPA | isopropanol, 2-propanol | LDA | lithium diisopropylamide |
| M | Molar | mmol | milimolar |
| mCPBA | meta-Chloroperoxy benzoic acid | Me | Methyl |
| MeCN | Acetonitrile | MeOH | Methanol |
| min | Minutes | mg | Milligrams |
| MHZ | Megahertz | mL (or ml) | Milliliter |
| Mol sieves | molecular sieves | N | normal |
| MTBE | Methyl tert-butyl ether | MPLC | Medium Pressure Liquid Chromatography/flash chromatography |
| NMR | Nuclear Magnetic Resonance | MS | Mass Spectroscopy |
| NBS | N-Bromosuccinimide | NMM | N-Methylmorpholine |
| NIS | N-iodosuccinimide | NMP | 1-methyl-2-pyrrolidone |
| ON | Overnight | PTLC | Preparative thin layer chromatography |
| PyBrOP | Bromo-tris-pyrrolidino-phosphonium hexafluorophosphate | pin | pinacol |
| PyBOP | (Benzotriazol-1-yloxy)tripyrrolidino-phosphonium hexa-fluorophosphate | Pyr | Pyridine |
| dtbpf | 1,1'-Bis(di-tert-butylphosphino)ferrocene | Ni(COD)$_2$ | Bis(1,5-cyclooctadiene)nickel(0) |
| Quant | quantitative | RT or rt | Room temperature |
| sat (or sat. or sat'd.) | Saturated | SFC | supercritical fluid chromatography |
| | | SiliaMetS ® DMT | Silica bound equivalent of 2,4,6-trimercaptotriazine (metal scavenger) |
| sgc | Silica gel 60 chromatography | SiO$_2$ | Silica gel |
| tBOC | tert-Butoxycarbonyl | t-Bu | tert-butyl |
| TEA | Triethylamine | Tf | Trifluoromethane sulfonyl |
| TFA | Trifluoro acetic acid | THF | Tetrahydrofuran |
| TLC | Thin layer chromatography | Ts | Toluene sulfonyl |
| SEM | 2-(Trimethylsilyl)ethoxy-methyl | Tr | Triphenylmethyl |
| | | Trityl | |
| TsOH | para-toluene sulfonic acid | TsOH•H$_2$O | para-toluene sulfonic acid hydrate |
| TBAF | Tetrabutylammonium fluoride | TBS | Tert-butyldimethyl silyl |
| T3P | n-propylphosphonic anhydride | PMB or p-MB | Para-methoxybenzyl |
| Xantphos | 4,5-Bis(diphenylphosphino)-9,9-dimethylxanthene | RuPhos | 2-Dicyclohexylphosphino-2',6'-diisopropoxybiphenyl |
| ~ | Approximately | | |

General Experimental Information:

Unless otherwise noted, all reactions are magnetically stirred.

Unless otherwise noted, when diethyl ether is used in the experiments described below, it is Fisher ACS certified material and is stabilized with BHT.

Unless otherwise noted, "concentrated to dryness" means evaporating the solvent from a solution or mixture using a rotary evaporator.

Unless otherwise noted, flash chromatography is carried out on an Isco, Analogix, or Biotage automated chromatography system using a commercially available cartridge as the column. Columns may be purchased from Isco, Analogix, Biotage, Varian, or Supelco and are usually filled with silica gel as the stationary phase.

Unless otherwise noted, all LRRK2 IC$_{50}$ data presented in tables refers to the LRRK2 Km ATP LanthaScreen™ Assay that is described in the Biological Assay section.

Scheme 1

Preparation of Example 1

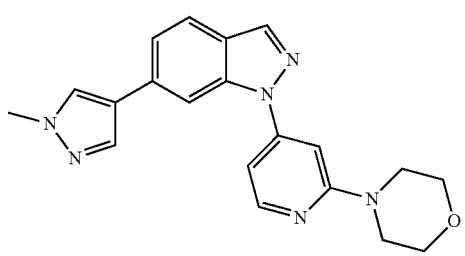 [SMILES: Cn1cc(-c2ccc3cnn(-c4ccnc(N5CCOCC5)c4)c3c2)cn1]

Step 1—Synthesis of 6-(1-methyl-1H-pyrazol-4-yl)-1H-indazole

Step 2—Synthesis of 4-(4-(6-(1-methyl-1H-pyrazol-4-yl)-1H-indazol-1-yl)pyridin-2-yl)morpholine

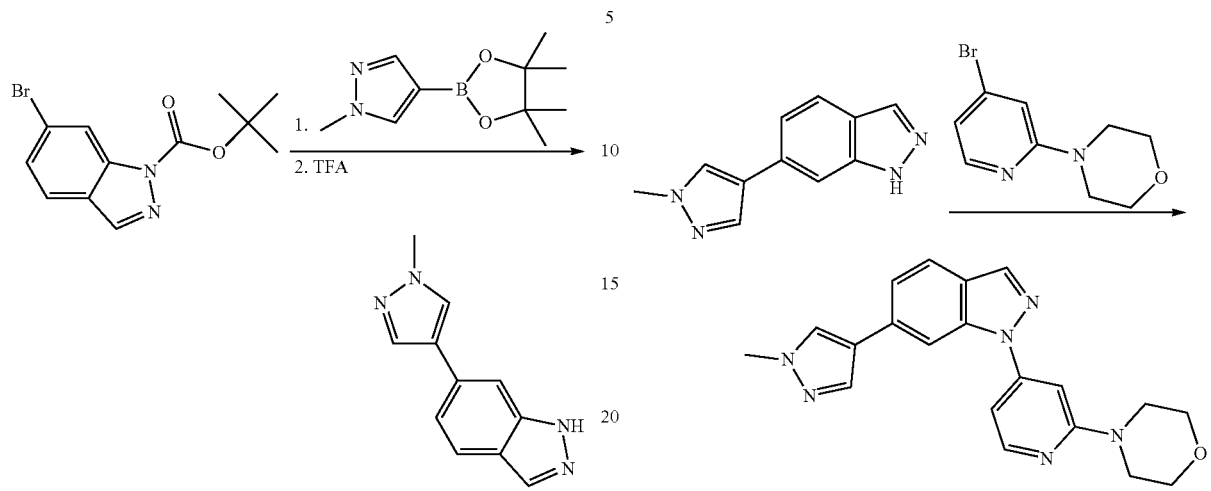

A mixture of tert-butyl 6-bromo-1H-indazole-1-carboxylate (400 mg, 1.34 mmol), 1-methyl-4-(4,4,5,5-tetramethyl-1,3,2-dioxaborolan-2-yl)-1H-pyrazole (420 mg, 2.02 mmol), bis(tri-t-butylphosphine)palladium(0) (220 mg, 0.27 mmol) and $K_2CO_3$ (372 mg, 2.69 mmol) in 1,4-dioxane (6 mL) and $H_2O$ (200 µL) was microwaved at 110° C. for 1 h and at 130° C. for 1 h. The filtration removed the solid and washed with DCM. The combined filtrate was concentrated in vacuo. The residue was treated with TFA (5 ml), stirred at rt for 30 min), concentrated in vacuo, basified by addition of 7N $NH_3$ in MeOH (10 ml) and purified by ISCO flash chromatography (eluted with 0-100% EtOAc/hexane) to provide 6-(1-methyl-1H-pyrazol-4-yl)-1H-indazole as the yellow solid.

A mixture of 6-(1-methyl-1H-pyrazol-4-yl)-1H-indazole (130 mg, 0.66 mmol), 4-(4-bromopyridin-2-yl)morpholine (319 mg, 1.31 mmol), copper(I) iodide (18 mg, 0.10 mmol), trans-N, N-dimethylcyclohexane-1,2-diamine (28 mg, 0.20 mmol) and $Cs_2CO_3$ (641 mg, 1.97 mmol) in DMF (3 mL) was microwaved at 120° C. for 6 h. The filtration removed the solid. After washing with DCM, the combined filtrate was concentrated in vacuo. The residue was purified by ISCO flash chromatography (eluted with 0-100% EtOAc/hexane) to provide 4-(4-(6-(1-methyl-1H-pyrazol-4-yl)-1H-indazol-1-yl)pyridin-2-yl)morpholine (Example 1). LCMS (ESI) m/z 361 (Ret.=1.90 min, LCMS method a); LRRK2 $IC_{50}$: 72 nM. Rat PK Oral AUC: 2.1+/−0.09 µM·h.

TABLE 1.1

Starting with indazole and utilizing the method outlined in Step 2 of Scheme 1, the following Example was prepared:

| Ex | Structure | LCMS m/z (method) | LRRK2 $IC_{50}$ (nM) | Rat AUC 10 mpk PO (µM · h) |
|---|---|---|---|---|
|  | IUPAC Name |  |  |  |
| 1 | 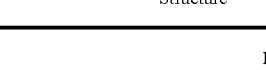 4-(4-(6-(1-methyl-1H-pyrazol-4-yl)-1H-indazol-1-yl)pyridin-2-yl)morpholine | 361 (a) | 72 | 2.1 +/− 0.09 |

TABLE 1.1-continued

Starting with indazole and utilizing the method outlined in Step 2 of Scheme 1, the following Example was prepared:

| Ex | Structure | LCMS m/z (method) | LRRK2 IC$_{50}$ (nM) | Rat AUC 10 mpk PO (µM · h) |
|---|---|---|---|---|
| 2 | 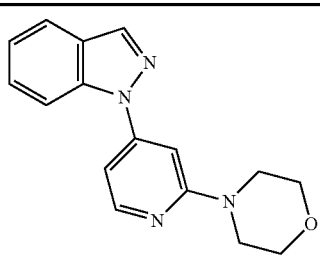 | 280 (a) | 633 | * |

4-(4-(1H-indazol-1-yl)pyridin-2-yl)morpholine

TABLE 1.2

Utilizing the method outlined in Steps 1 and 2 of Scheme 1, the following Example was prepared:

| Ex | Structure | LCMS m/z (method) | LRRK2 IC$_{50}$ (nM) | Rat AUC 10 mpk PO (µM · h) |
|---|---|---|---|---|
| | IUPAC Name | | | |
| 3 | 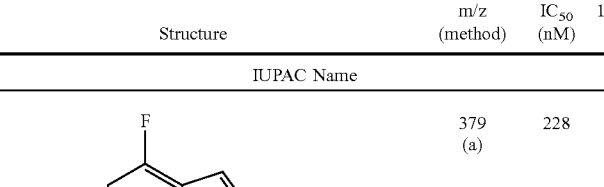 | 379 (a) | 228 | * |

4-(4-(4-fluoro-6-(1-methyl-1H-pyrazol-4-yl)-1H-indazol-1-yl)pyridin-2-yl)morpholine Scheme 2

Preparation of Example 4

Synthesis of 4-(4-(6-isopropoxy-1H-indazol-1-yl)pyridin-2-yl)morpholine

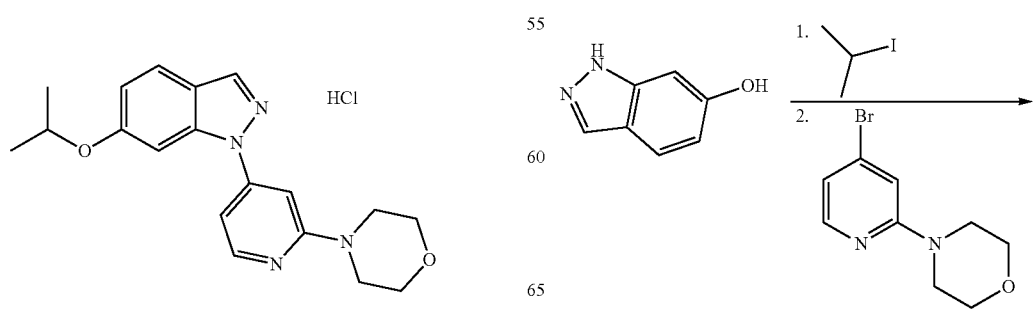

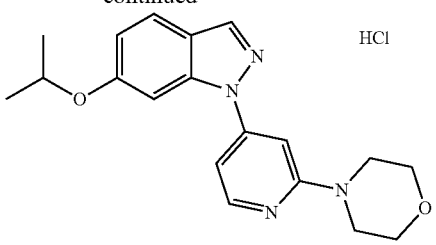

A mixture of 1H-indazol-6-ol (124 mg, 0.96 mmol) and Cs$_2$CO$_3$ (804 mg, 2.47 mmol) in DMF (3 mL) was added 2-iodopropane (157 mg, 0.93 mmol), stirred at rt for 6 h and at 50° C. for 1 h, followed by addition of copper(I) iodide (23 mg, 0.12 mmol) and trans-N, N-dimethylcyclohexane-1,2-diamine (35 mg, 0.25 mmol). The resulting mixture was microwaved at 120° C. for 6 h. The filtration removed the solid. After washing with DCM, the combined filtrate was concentrated in vacuo. The residue was purified by ISCO flash chromatography (eluted with 0-100% EtOAc/hexane) to provide 4-(4-(6-isopropoxy-1H-indazol-1-yl)pyridin-2-yl)morpholine (150 mg) which was dissolved in EtOAc (3 ml), treated with 4N HCl in dioxane (3 mL) and stirred for 5 min. The volatiles were evaporated in vacuo and the residue was washed with ether. The filtration collected HCl salt (Example 4). LCMS (ESI) m/z 339 (Ret.=2.03 min, LCMS method a); LRRK2 IC$_{50}$: 122 nM.

| Ex | Structure | LCMS m/z (method) | LRRK2 IC$_{50}$ (nM) | Rat AUC 10 mpk PO (μM · h) |
|---|---|---|---|---|
| | IUPAC Name | | | |
| 4 | 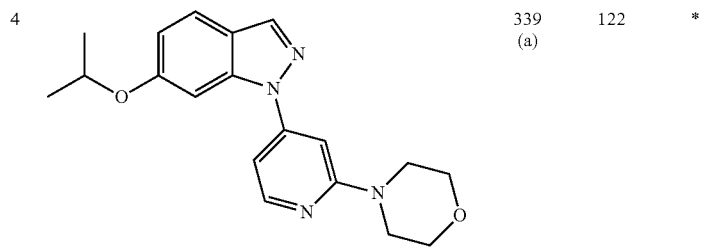 | 339 (a) | 122 | * |
| | 4-(4-(6-isopropoxy-1H-indazol-1-yl)pyridin-2-yl)morpholine hydrochloride | | | |
| 5 | This space intentionally left blank | * | * | * |

Scheme 3

Preparation of Example 6

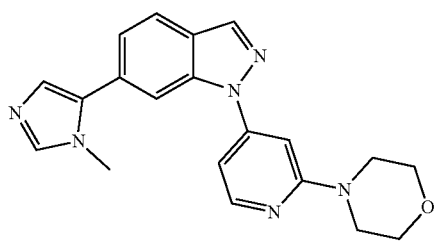 [SMILES: Cn1cncc1-c1ccc2cnn(-c3ccnc(N4CCOCC4)c3)c2c1]

Step 1—Synthesis of 6-(1-methyl-1H-imidazol-5-yl)-1H-indazole

Step 2—Synthesis of 4-(4-(6-(1-methyl-1H-imidazol-5-yl)-1H-indazol-1-yl)pyridin-2-yl)morpholine

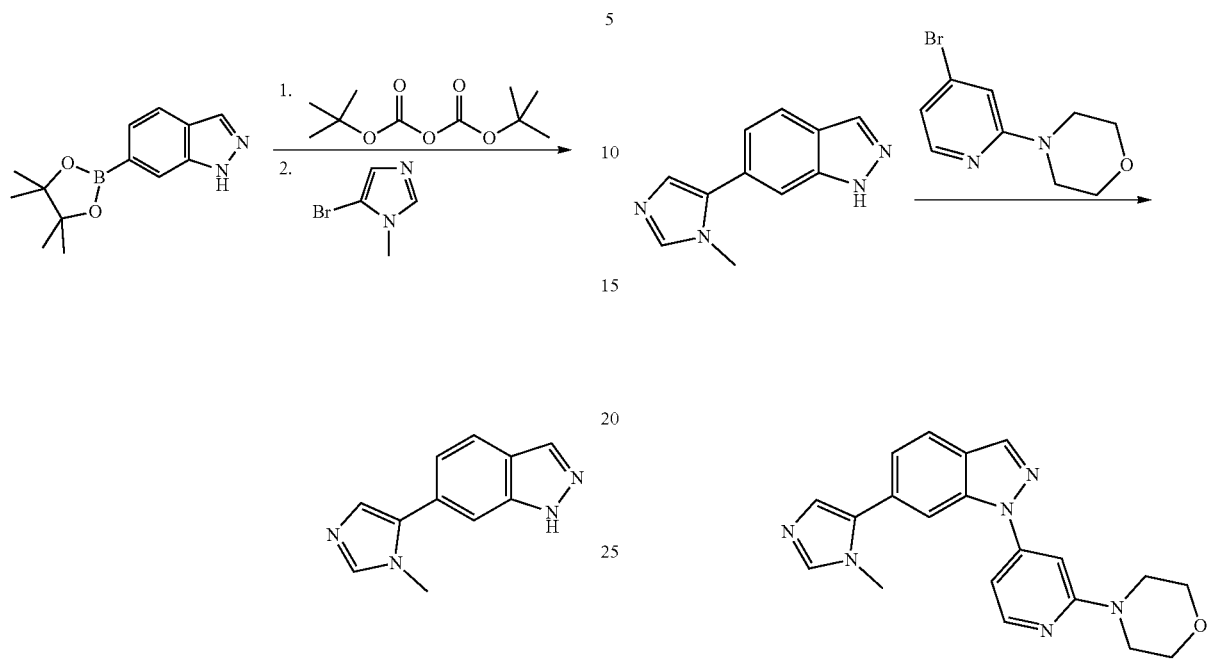

To a solution of 6-(4,4,5,5-tetramethyl-1,3,2-dioxaborolan-2-yl)-1H-indazole (500 mg, 2.05 mmol) in 1,4-dioxane (8 mL) was added $K_2CO_3$ (566 mg, 4.10 mmol) and di-tert-butyl dicarbonate (671 mg, 0.41 mmol). The mixture was stirred at rt for 3 h, then added 5-bromo-1-methyl-1H-imidazole (495 mg, 3.07 mmol), H2O (200 μL) and bis(tri t-butylphophine)palladium(0) (300 mg, 0.27 mmol). The reaction was heated to 110° C. and stirred overnight. The filtration removed the solid and washed with DCM. The combined filtrate was concentrated in vacuo. The resulting residue was purified using preparative TLC (eluted with 4% MeOH/DCM) to provide 6-(1-methyl-1H-imidazol-5-yl)-1H-indazole as the yellow solid.

A mixture of 6-(1-methyl-1H-imidazol-5-yl)-1H-indazole (155 mg, 0.78 mmol), $Cs_2CO_3$ (510 mg, 1.56 mmol), copper (I) iodide (30 mg, 0.16 mmol) and trans-N, N-dimethylcyclohexane-1,2-diamine (45 mg, 0.31 mmol) in DMF (3 mL) was microwaved at 120° C. for 6 h. The filtration removed the solid. After washing with DCM, the combined filtrate was concentrated in vacuo. The residue was purified by ISCO flash chromatography (eluted with 0-100% EtOAc/hexane) to provide 4-(4-(6-(1-methyl-1H-imidazol-5-yl)-1H-indazol-1-yl)pyridin-2-yl)morpholine (Example 6). LCMS (ESI) m/z 361 (Ret.=1.65 min, LCMS method a); LRRK2 $IC_{50}$: 119 nM.

| Ex | Structure | LCMS m/z (method) | LRRK2 $IC_{50}$ (nM) | Rat AUC 10 mpk PO (μM · h) |
|---|---|---|---|---|
| | IUPAC Name | | | |
| 6 | 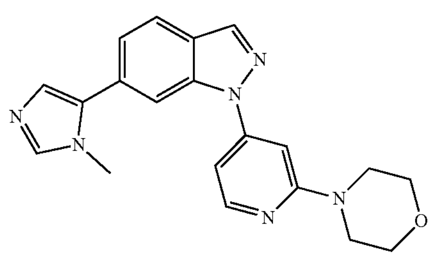 [SMILES: Cn1cncc1-c1ccc2cnn(-c3ccnc(N4CCOCC4)c3)c2c1] | 361 (a) | 119 | * |
| | 4-(4-(6-(1-methyl-1H-imidazol-5-yl)-1H-indazol-1-yl)pyridin-2-yl)morpholine | | | |
| 7 | This space intentionally left blank | * | * | * |

Scheme 5

Preparation of Example 8

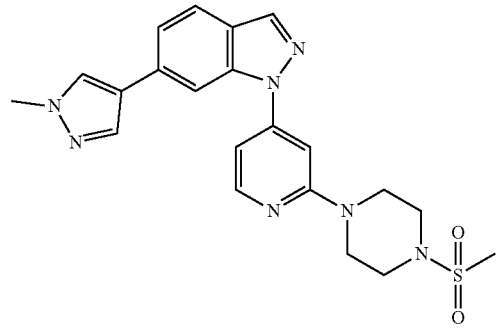

Synthesis of 6-(1-methyl-1H-pyrazol-4-yl)-1-(2-(4-(methylsulfonyl)piperazin-1-yl)pyridin-4-yl)-1H-indazole

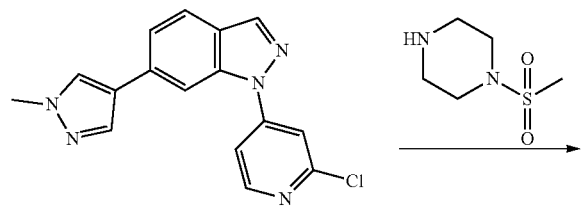

-continued

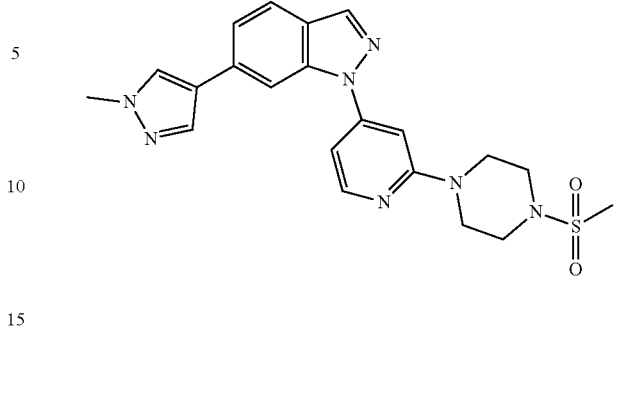

To a solution of 1-(2-chloropyridin-4-yl)-6-(1-methyl-1H-pyrazol-4-yl)-1H-indazole (50 mg, 0.16 mmol) and 1-(methylsulfonyl)piperazine (40 mg, 0.24 mmol) in 1,4-dioxane (2 mL) was added Bis(1,5-cyclooctadiene)nickel(0) (9 mg, 0.03 mmol), 1,3-Bis-(2,6-diisopropylphenyl) imidazolinium chloride (21 mg, 0.05 mmol) and sodium tert-butoxide (47 mg, 0.48 mmol). The resulting mixture was heated to 80° C. and stirred for 2 h. The filtration removed the solid. After washing with DCM, the combined filtrate was concentrated in vacuo. The residue was purified by ISCO flash chromatography (eluted with 0-4% MeOH/DCM) to provide 6-(1-methyl-1H-pyrazol-4-yl)-1-(2-(4-(methylsulfonyl)piperazin-1-yl)pyridin-4-yl)-1H-indazole (Example 8). LCMS (ESI) m/z 438 (Ret.=1.93 min, LCMS method a); LRRK2 $IC_{50}$: 45 nM. Rat PK Oral AUC: 41+/−26 μM·h.

| Ex | Structure | LCMS m/z (method) | LRRK2 $IC_{50}$ (nM) | Rat AUC 10 mpk PO (μM · h) |
|---|---|---|---|---|
| | IUPAC Name | | | |
| 8 | 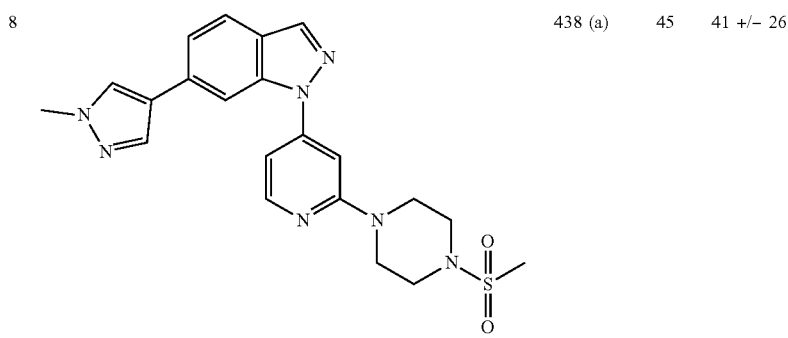 | 438 (a) | 45 | 41 +/− 26 |
| | 6-(1-methyl-1H-pyrazol-4-yl)-1-(2-(4-(methylsulfonyl)piperazin-1-yl)pyridin-4-yl)-1H-indazole | | | |

Examples 9 to 16, depicted in the table below, were prepared using the method described above.

| Ex | Structure | LCMS m/z (method) | LRRK2 IC$_{50}$ (nM) | Rat AUC 10 mpk PO (μM · h) |
|---|---|---|---|---|
| | IUPAC Name | | | |
| 9 | 6-(1-methyl-1H-pyrazol-4-yl)-1-(2-(4-methylpiperazin-1-yl)pyridin-4-yl)-1H-indazole | 374 (a) | 56 | * |
| 10 | 1-methyl-4-(4-(6-(1-methyl-1H-pyrazol-4-yl)-1H-indazol-1-yl)pyridin-2-yl)piperazin-2-one | 388 (a) | 126 | * |
| 11 | 1-(2-(3,3-difluoroazetidin-1-yl)pyridin-4-yl)-6-(1-methyl-1H-pyrazol-4-yl)-1H-indazole | 367 (a) | 224 | * |
| 12 | (R)-1-(2-(3-fluoropyrrolidin-1-yl)pyridin-4-yl)-6-(1-methyl-1H-pyrazol-4-yl)-1H-indazole | 363 (a) | 89 | 0.82 +/− 0.35 |

-continued

| Ex | Structure | LCMS m/z (method) | LRRK2 IC$_{50}$ (nM) | Rat AUC 10 mpk PO (μM·h) |
|---|---|---|---|---|
| 13 | (S)-1-(2-(3-fluoropyrrolidin-1-yl)pyridin-4-yl)-6-(1-methyl-1H-pyrazol-4-yl)-1H-indazole | 363 (a) | 108 | * |
| 14 | 1-(2-(3-fluoroazetidin-1-yl)pyridin-4-yl)-6-(1-methyl-1H-pyrazol-4-yl)-1H-indazole | 349 (a) | 145 | * |
| 15 | tert-butyl 4-(4-(6-(1-methyl-1H-pyrazol-4-yl)-1H-indazol-1-yl)pyridin-2-yl)piperazine-1-carboxylate | 460 (a) | 34 | * |
| 16 | 6-(1-methyl-1H-pyrazol-4-yl)-1-(2-(4-(methylsulfonyl)piperidin-1-yl)pyridin-4-yl)-1H-indazole | 437 (a) | 128 | * |

Scheme 6

Preparation of Example 17

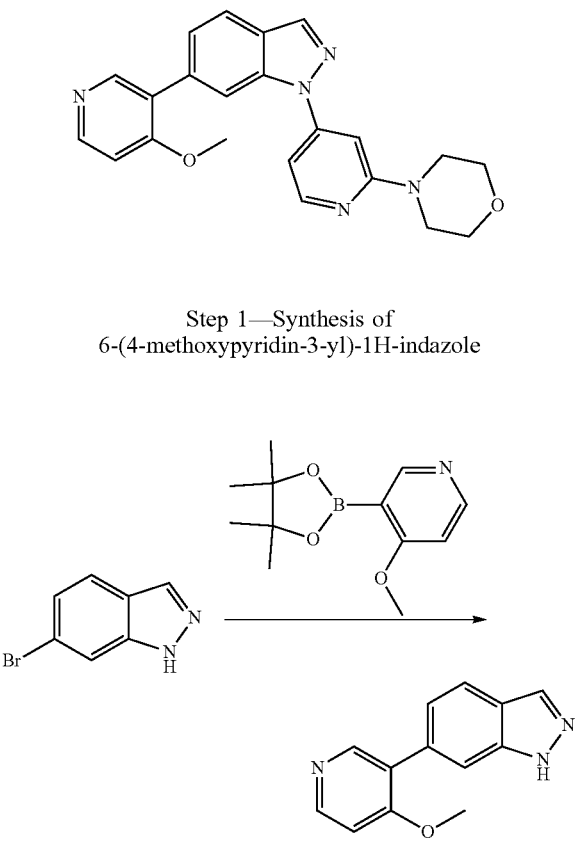

Step 1—Synthesis of
6-(4-methoxypyridin-3-yl)-1H-indazole

A mixture of 6-bromo-1H-indazole (500 mg, 2.54 mmol), 4-methoxy-3-(4,4,5,5-tetramethyl-1,3,2-dioxaborolan-2-yl)pyridine (895 mg, 3.81 mmol), Pd(dppf)Cl2 (414 mg, 0.51 mmol) and $K_2CO_3$ (701 mg, 5.08 mmol) in dioxane (10 mL) and water (0.5 mL) was heated to 110° C. and stirred overnight. The filtration removed the solid. After washing with DCM, the combined filtrate was concentrated in vacuo. The residue was purified by ISCO flash chromatography (eluted with 0-100% EtOAc/hexane) to provide 6-(4-methoxypyridin-3-yl)-1H-indazole.

Step 2—Synthesis of 4-(4-(6-(4-methoxypyridin-3-yl)-1H-indazol-1-yl)pyridin-2-yl)morpholine

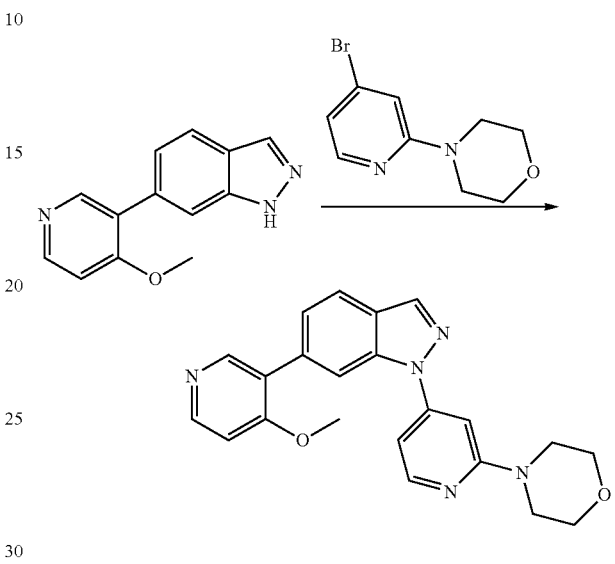

A mixture of 6-(4-methoxypyridin-3-yl)-1H-indazole (100 mg, 0.44 mmol), 4-(4-bromopyridin-2-yl)morpholine (162 mg, 0.67 mmol), $Pd_2(dba)_3$ (41 mg, 0.04 mmol), 2-di-tert-butylphosphino-2',4',6'-triisopropylbiphenyl (38 mg, 0.09 mmol) and sodium tert-butoxide (64 mg, 0.67 mmol) in toluene (3 mL) was heated to 85° C. and stirred for 4 h. The filtration removed the solid. After washing with DCM, the combined filtrate was concentrated in vacuo. The residue was purified by ISCO flash chromatography (eluted with 0-5% MeOH/DCM) to provide 4-(4-(6-(4-methoxypyridin-3-yl)-1H-indazol-1-yl)pyridin-2-yl)morpholine (Example 17). LCMS (ESI) m/z 388 (Ret.=1.73 min, LCMS method a); LRRK2 $IC_{50}$: 43 nM. Rat PK Oral AUC: 10+/−2.5 μM·h.

| Ex | Structure | LCMS m/z (method) | LRRK2 $IC_{50}$ (nM) | Rat AUC 10 mpk PO (μM · h) |
|---|---|---|---|---|
| | IUPAC Name | | | |
| 17 | 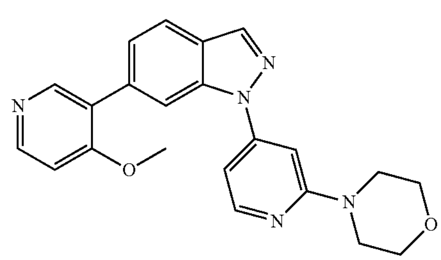 [SMILES: COc1ccncc1-c1ccc2cnn(-c3ccnc(N4CCOCC4)c3)c2c1] | 388 (a) | 43 | 10 +/− 2.5 |
| | 4-(4-(6-(4-methoxypyridin-3-yl)-1H-indazol-1-yl)pyridin-2-yl)morpholine | | | |

Scheme 7

Preparation of Example 18

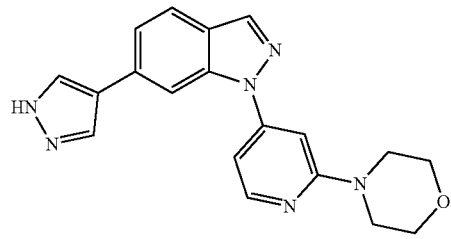

Step 1—Synthesis of
6-(1-trityl-1H-pyrazol-4-yl)-1H-indazole

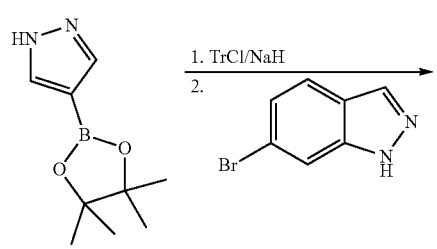

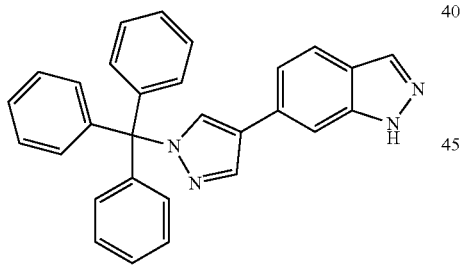

To solution of 4-(4,4,5,5-tetramethyl-1,3,2-dioxaborolan-2-yl)-1H-pyrazole (941 mg, 4.87 mmol) in 1,4-dioxane (8 mL) was added NaH (219 mg, 5.48 mmol) and stirred at rt for 10 min, followed by addition TrCl (1.36 g, 4.87 mmol). The resulting mixture was stirred at rt for 2 h, then added H$_2$O (200 μL), K2CO3 (842 mg, 6.09 mmol), 6-bromo-1H-indazole (600 mg, 3.05 mmol) and Pd(dppf)Cl2 (446 mg, 0.11 mmol). Heated to 110° C. and stirred overnight. The filtration removed the solid and washed with DCM. The combined filtrate was concentrated in vacuo. The residue was purified by ISCO flash chromatography (eluted with 0-100% EtOAc/hexane) to provide 6-(1-trityl-1H-pyrazol-4-yl)-1H-indazole as the yellow solid.

Step 2—Synthesis of 4-(4-(6-(1-trityl-1H-pyrazol-4-yl)-1H-indazol-1-yl)pyridin-2-yl)morpholine

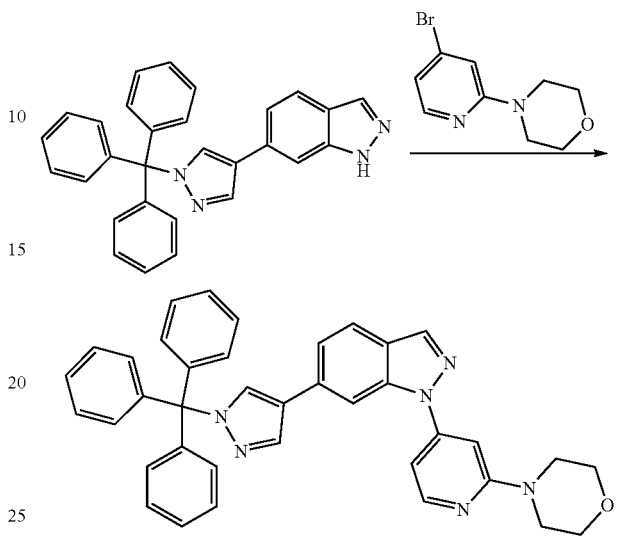

A mixture of 6-(1-trityl-1H-pyrazol-4-yl)-1H-indazole (344 mg, 0.81 mmol), 4-(4-bromopyridin-2-yl)morpholine (294 mg, 1.21 mmol), Pd$_2$(dba)$_3$ (148 mg, 0.16 mmol), 2-di-tert-butylphosphino-2',4',6'-triisopropylbiphenyl (103 mg, 0.24 mmol) and sodium tert-butoxide (155 mg, 0.61 mmol) in toluene (8 mL) was heated to 80° C. and stirred overnight. The filtration removed the solid. After washing with DCM, the combined filtrate was concentrated in vacuo. The residue was purified by ISCO flash chromatography (eluted with 0-5% MeOH/DCM) to provide 4-(4-(6-(1-trityl-1H-pyrazol-4-yl)-1H-indazol-1-yl)pyridin-2-yl)morpholine.

Step 3—Synthesis of 4-(4-(6-(1-trityl-1H-pyrazol-4-yl)-1H-indazol-1-yl)pyridin-2-yl)morpholine

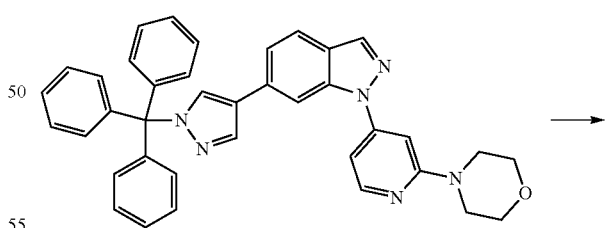

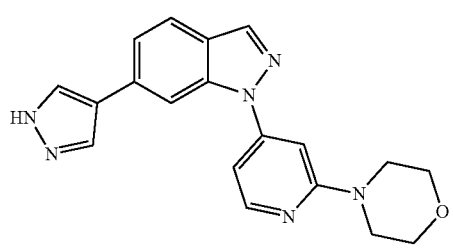 [SMILES: c1cc(-n2ncc3ccc(-c4cn[nH]c4)cc32)cc(N2CCOCC2)n1]

A mixture of 4-(4-(6-(1-trityl-1H-pyrazol-4-yl)-1H-indazol-1-yl)pyridin-2-yl)morpholine (400 mg, 0.68 mmol), TFA (3 mL) and triethylsilane (1 mL) was stirred at rt for 2 h and concentrated in vacuo. The residue was basified by addition of 7N NH$_3$ in MeOH (10 mL) and purified by preparative TLC (eluted with 0-5% MeOH/DCM) to provide 4-(4-(6-(1H-pyrazol-4-yl)-1H-indazol-1-yl)pyridin-2-yl)morpholine (Example 18). LCMS (ESI) m/z 347 (Ret.=1.88 min, LCMS method a); LRRK2 IC$_{50}$: 73 nM.

| Ex | Structure | LCMS m/z (method) | LRRK2 IC$_{50}$ (nM) | Rat AUC 10 mpk PO (μM · h) |
|---|---|---|---|---|
| | IUPAC Name | | | |
| 18 | 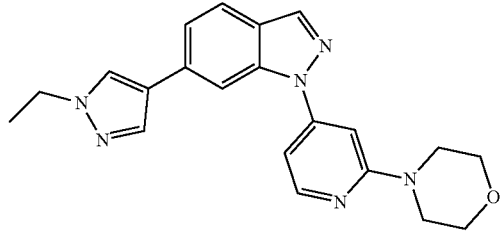 [SMILES: CCn1cc(-c2ccc3cnn(-c4ccnc(N5CCOCC5)c4)c3c2)cn1] | 347 (a) | 73 | * |
| | 4-(4-(6-(1-trityl-1H-pyrazol-4-yl)-1H-indazol-1-yl)pyridin-2-yl)morpholine | | | |

Scheme 8

Preparation of Example 19

Synthesis of 4-(4-(6-(1-ethyl-1H-pyrazol-4-yl)-1H-indazol-1-yl)pyridin-2-yl)morpholine

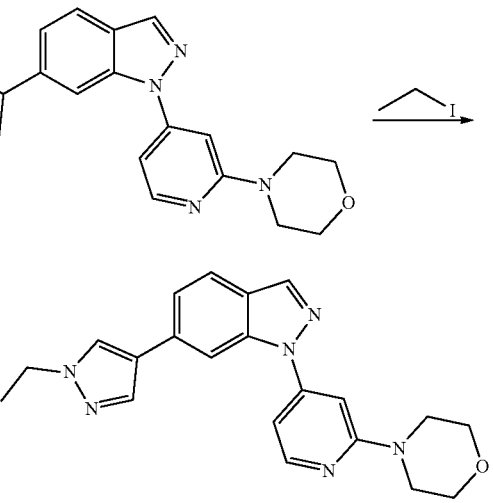

To a solution of 4-(4-(6-(1H-pyrazol-4-yl)-1H-indazol-1-yl)pyridin-2-yl)morpholine (40 mg, 0.12 mmol) in DMF (1 ml) was NaH (9.3 mg, 0.23 mmol) and stirred at rt for 10 min, followed by addition of iodoethane (36 mg, 0.23 mmol). The resulting mixture was stirred at rt for 3 h. The volatiles were evaporated in vacuo and the residue was purified by ISCO flash chromatography (eluted with 0-5% MeOH/DCM) to provide 4-(4-(6-(1-ethyl-1H-pyrazol-4-yl)-1H-indazol-1-yl)pyridin-2-yl)morpholine (Example 19). LCMS (ESI) m/z 375 (Ret.=2.01 min, LCMS method a); LRRK2 IC$_{50}$: 128 nM

| Ex | Structure | LCMS m/z (method) | LRRK2 IC$_{50}$ (nM) | Rat AUC 10 mpk PO (µM · h) |
|---|---|---|---|---|
| | IUPAC Name | | | |
| 19 | 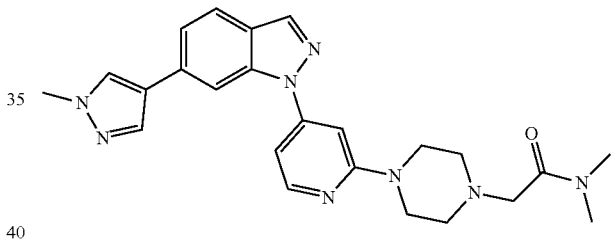 4-(4-(6-(1-ethyl-1H-pyrazol-4-yl)-1H-indazol-1-yl)pyridin-2-yl)morpholine | 375 (a) | 128 | * |

Scheme 9

Preparation of Example 20

Synthesis of N,N-dimethyl-2-(4-(4-(6-(1-methyl-1H-pyrazol-4-yl)-1H-indazol-1-yl)pyridin-2-yl)piperazin-1-yl)acetamide

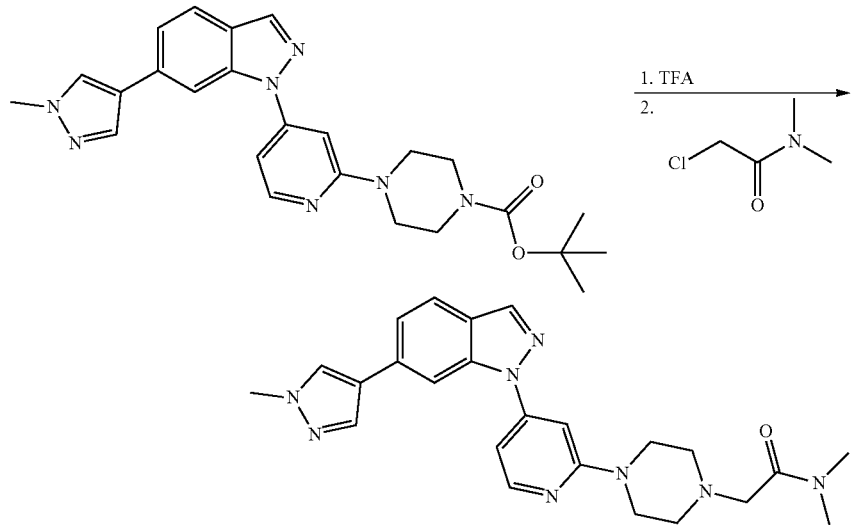

A solution of tert-butyl 4-(4-(6-(1-methyl-1H-pyrazol-4-yl)-1H-indazol-1-yl)pyridin-2-yl)piperazine-1-carboxylate (250 mg, 0.54 mmol) in TFA (2 mL) was stirred at rt for 3 h and concentrated in vacuo. 1,4-dioxane (4 mL) was added, followed by addition of 2-chloro-N,N-dimethylacetamide (397 mg, 3.26 mmol) and K$_2$CO$_3$ (451 mg, 3.26 mmol). The mixture was heated to 100° C. and stirred for 6 h. The filtration removed the solid. After washing with DCM, the combined filtrate was concentrated in vacuo. The residue was purified by ISCO flash chromatography (eluted with 0-5% MeOH/DCM) to provide N,N-dimethyl-2-(4-(4-(6-(1-methyl-1H-pyrazol-4-yl)-1H-indazol-1-yl)pyridin-2-yl)piperazin-1-yl)acetamide (Example 20). LCMS (ESI) m/z 445 (Ret.=1.83 min, LCMS method a). LRRK2 IC$_{50}$: 34 nM. Rat PK Oral AUC: 1.0+/−0.19 μM·h.

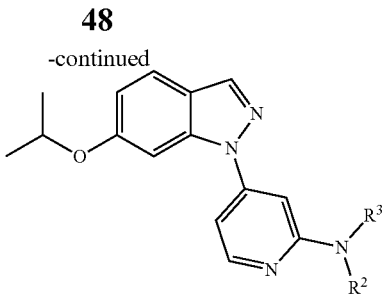

To a set of 2 dram vials equipped with stir bars was added the requisite amine (0.17 mmol) if it was a solid followed by 1,3-bis(2,6-diisopropylphenyl)imidazolium chloride (7.4 mg, 0.017 mmol), Pd$_2$dba$_3$ (4 mg, 0.004 mmol) and NaOt-Bu (33 mg, 0.35 mmol). The vials were then transferred into a glove bag under an atmosphere of nitrogen. At this time the requisite liquid amines (0.17 mmol) were added to the appropriate vials. To each vial was added a solution of Compound 1-(2-chloropyridin-4-yl)-6-isopropoxy-1H-indazole (25 mg, 0.087 mmol) in dioxane (1 mL). The vials were then capped and removed from the glove bag and placed into a preheated aluminum block at 90° C. The mixtures were stirred at that temperature overnight. The vials were then allowed to cool to RT. To each vial was added DCM (2 mL) followed by water (1 mL). The organic layer was separated and filtered into a clean set of vials. The solvent was then removed under reduced pressure. The crude residues were dissolved in DMSO (1 mL) and filtered. The crude products were purified by mass triggered HPLC using the following conditions: [Waters XBridge C18 column, 5 μm, 19×100 mm, gradient ranges from 5-50% initial to 35-95% final MeCN (0.1% NH$_4$OH) in water (0.1% NH$_4$OH) 50 mL/min, 8-15 min run time] to afford the desired compounds.

Examples 23~55, depicted in the table below, were prepared using the method described above.

| Ex | Structure | LCMS m/z (method) | LRRK2 IC$_{50}$ (nM) | Rat AUC 10 mpk PO (μM · h) |
|---|---|---|---|---|
| | IUPAC Name | | | |
| 20 | (structure shown) | 445 (a) | 34 | 1.0 +/− 0.19 |
| | N,N-dimethyl-2-(4-(4-(6-(1-methyl-1H-pyrazol-4-yl)-1H-indazol-1-yl)pyridin-2-yl)piperazin-1-yl)acetamide | | | |
| 21 | This space intentionally left blank* | * | * | * |
| 22 | This space intentionally left blank* | * | * | * |

Scheme 10

Preparation of Examples 23-55

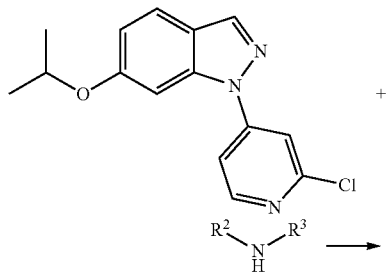

| Ex | Structure | LCMS m/z (method) | LRRK2 IC$_{50}$ (nM) | Rat AUC 10 mpk PO (μM·h) |
|---|---|---|---|---|
| | IUPAC Name | | | |
| 23 | 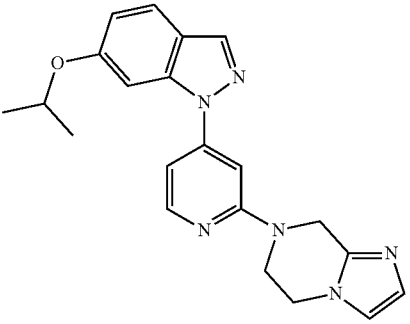 [SMILES: CC(C)Oc1ccc2cnn(-c3ccnc(N4CCn5ccnc5C4)c3)c2c1] | 374 (b) | 446 | * |
| | 7-(4-(6-isopropoxy-1H-indazol-1-yl)pyridin-2-yl)-5,6,7,8-tetrahydroimidazo[1,2-a]pyrazine | | | |
| 24 | 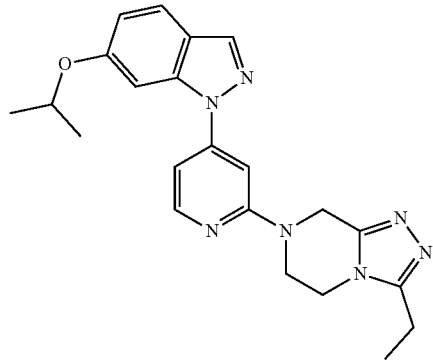 [SMILES: CCc1nnc2n1CCN(c1cc(-n3ncc4ccc(OC(C)C)cc43)ccn1)C2] | 403 (b) | 435 | * |
| | 3-ethyl-7-(4-(6-isopropoxy-1H-indazol-1-yl)pyridin-2-yl)-5,6,7,8-tetrahydro-[1,2,4]triazolo[4,3-a]pyrazine | | | |
| 25 | 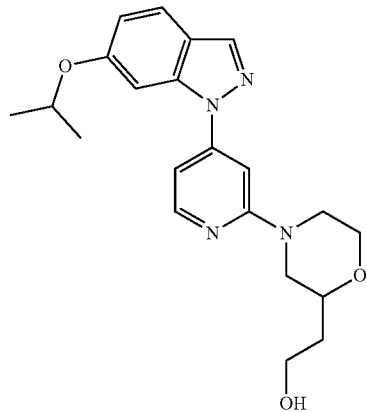 [SMILES: CC(C)Oc1ccc2cnn(-c3ccnc(N4CCOC(CCO)C4)c3)c2c1] | 382 (b) | 412 | * |
| | 2-(4-(4-(6-isopropoxy-1H-indazol-1-yl)pyridin-2-yl)morpholin-2-yl)ethanol | | | |
| 26 | 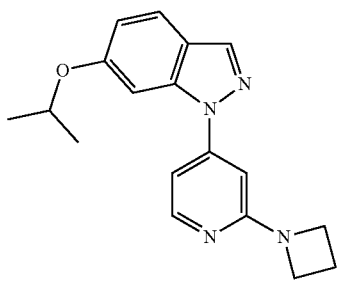 [SMILES: CC(C)Oc1ccc2cnn(-c3ccnc(N4CCC4)c3)c2c1] | 308 (b) | 584 | * |

-continued
| Ex | Structure | LCMS m/z (method) | LRRK2 IC$_{50}$ (nM) | Rat AUC 10 mpk PO (μM · h) |
|---|---|---|---|---|
1-(2-(azetidin-1-yl)pyridin-4-yl)-6-isopropoxy-1H-indazole
| 27 | 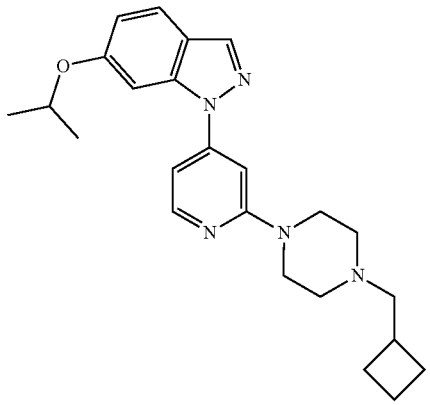 [SMILES: CC(C)Oc1ccc2cnn(-c3ccnc(N4CCN(CC5CCC5)CC4)c3)c2c1] | 405 (b) | 362 | * |
1-(2-(4-(cyclobutylmethyl)piperazin-1-yl)pyridin-4-yl)-6-isopropoxy-1H-indazole
| 28 | 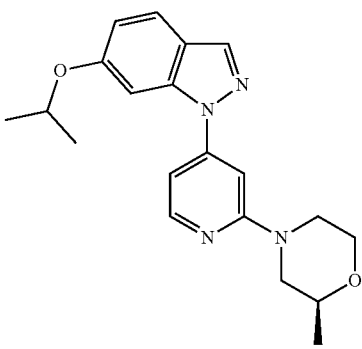 [SMILES: CC(C)Oc1ccc2cnn(-c3ccnc(N4CCO[C@@H](C)C4)c3)c2c1] | 352 (b) | 612 | * |
(S)-4-(4-(6-isopropoxy-1H-indazol-1-yl)pyridin-2-yl)-2-methylmorpholine
| 29 | 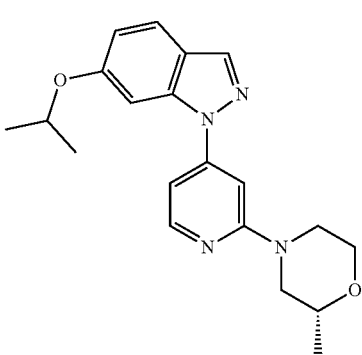 [SMILES: CC(C)Oc1ccc2cnn(-c3ccnc(N4CCO[C@H](C)C4)c3)c2c1] | 352 (b) | 490 | * |
(R)-4-(4-(6-isopropoxy-1H-indazol-1-yl)pyridin-2-yl)-2-methylmorpholine -continued

| Ex | Structure | LCMS m/z (method) | LRRK2 IC$_{50}$ (nM) | Rat AUC 10 mpk PO (μM · h) |
|---|---|---|---|---|
| 30 | 2-(1-(4-(6-isopropoxy-1H-indazol-1-yl)pyridin-2-yl)azetidin-3-yl)propan-2-ol | 366 (b) | 418 | * |
| 31 | 4-(4-(6-isopropoxy-1H-indazol-1-yl)pyridin-2-yl)-1-methylpiperazin-2-one | 365 (b) | 443 | * |
| 32 | cis-4-(4-(6-isopropoxy-1H-indazol-1-yl)pyridin-2-yl)-2,6-dimethylmorpholine | 366 (b) | 245 | * |
| 33 | 6-isopropoxy-1-(2-(4-(pyrimidin-2-yl)piperazin-1-yl)pyridin-4-yl)-1H-indazole | 415 (b) | 326 | * |

-continued
| Ex | Structure | LCMS m/z (method) | LRRK2 IC$_{50}$ (nM) | Rat AUC 10 mpk PO (μM · h) |
|---|---|---|---|---|
| 34 | 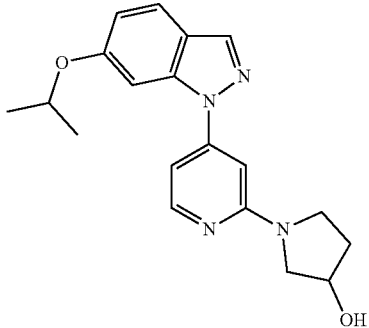 [SMILES: CC(C)Oc1ccc2cnn(-c3ccnc(N4CCC(O)C4)c3)c2c1]<br>1-(4-(6-isopropoxy-1H-indazol-1-yl)pyridin-2-yl)pyrrolidin-3-ol | 338 (b) | 307 | * |
| 35 | 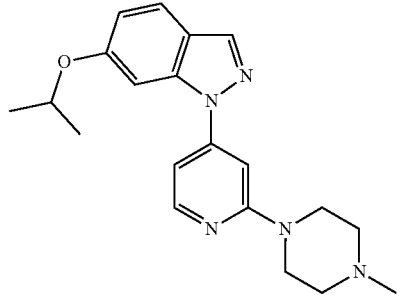 [SMILES: CC(C)Oc1ccc2cnn(-c3ccnc(N4CCN(C)CC4)c3)c2c1]<br>6-isopropoxy-1-(2-(4-methylpiperazin-1-yl)pyridin-4-yl)-1H-indazole | 351 (b) | 181 | * |
| 36 | 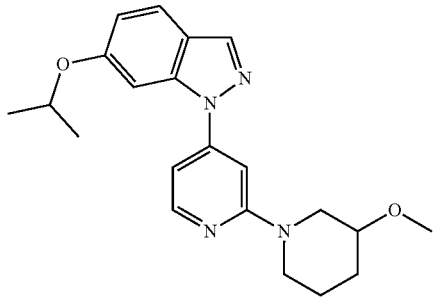 [SMILES: COC1CCCN(c2cc(-n3ncc4ccc(OC(C)C)cc43)ccn2)C1]<br>6-isopropoxy-1-(2-(3-methoxypiperidin-1-yl)pyridin-4-yl)-1H-indazole | 366 (b) | 596 | * |
| 37 | 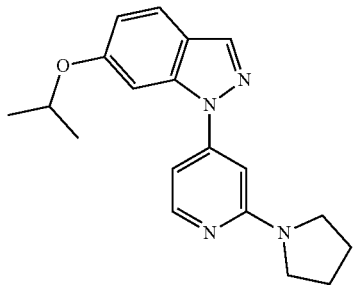 [SMILES: CC(C)Oc1ccc2cnn(-c3ccnc(N4CCCC4)c3)c2c1]<br>6-isopropoxy-1-(2-(pyrrolidin-1-yl)pyridin-4-yl)-1H-indazole | 322 (b) | 229 | * |

-continued

| Ex | Structure | LCMS m/z (method) | LRRK2 IC$_{50}$ (nM) | Rat AUC 10 mpk PO (μM · h) |
|---|---|---|---|---|
| 38 | 6-isopropoxy-1-(2-(piperidin-1-yl)pyridin-4-yl)-1H-indazole | 366 (b) | 835 | * |
| 39 | 2-(4-(4-(6-isopropoxy-1H-indazol-1-yl)pyridin-2-yl)piperazin-1-yl)ethanol | 381 (b) | 193 | * |
| 40 | 1-(4-(6-isopropoxy-1H-indazol-1-yl)pyridin-2-yl)piperidin-4-ol | 352 (b) | 378 | * |
| 41 | 6-isopropoxy-1-(2-(3-methoxy-3-methylazetidin-1-yl)pyridin-4-yl)-1H-indazole | 352 (b) | 890 | * |

-continued

| Ex | Structure | LCMS m/z (method) | LRRK2 IC$_{50}$ (nM) | Rat AUC 10 mpk PO (μM · h) |
|---|---|---|---|---|
| 42 | (R)-1-(2-(3-fluoropyrrolidin-1-yl)pyridin-4-yl)-6-isopropoxy-1H-indazole | 340 (b) | 412 | * |
| 43 | (S)-1-(2-(3-fluoropyrrolidin-1-yl)pyridin-4-yl)-6-isopropoxy-1H-indazole | 340 (b) | 950 | * |
| 44 | 1-(4-(6-(1-methyl-1H-pyrazol-4-yl)-1H-indazol-1-yl)pyridin-2-yl)piperidin-4-ol | 374 (b) | 100 | * |
| 45 | 6-(1-methyl-1H-pyrazol-4-yl)-1-(2-(pipendin-1-yl)pyridin-4-yl)-1H-indazole | 358 (b) | 141 | * |

| Ex | Structure | LCMS m/z (method) | LRRK2 IC$_{50}$ (nM) | Rat AUC 10 mpk PO (μM · h) |
|---|---|---|---|---|
| 46 | 6-(1-methyl-1H-pyrazol-4-yl)-1-(2-(pyrrolidin-1-yl)pyridin-4-yl)-1H-indazole | 344 (b) | 74 | * |
| 47 | cis-2,6-dimethyl-4-(4-(6-(1-methyl-1H-pyrazol-4-yl)-1H-indazol-1-yl)pyridin-2-yl)morpholine | 388 (b) | 32 | * |
| 48 | (3S,4S)-4-methoxy-1-(4-(6-(1-methyl-1H-pyrazol-4-yl)-1H-indazol-1-yl)pyridin-2-yl)pyrrolidin-3-ol | 390 (b) | 399 | * |
| 49 | (R)-2-methyl-4-(4-(6-(1-methyl-1H-pyrazol-4-yl)-1H-indazol-1-yl)pyridin-2-yl)morpholine | 374 (b) | 89 | * |

-continued

| Ex | Structure | LCMS m/z (method) | LRRK2 IC$_{50}$ (nM) | Rat AUC 10 mpk PO (μM · h) |
|---|---|---|---|---|
| 50 | (S)-2-methyl-4-(4-(6-(1-methyl-1H-pyrazol-4-yl)-1H-indazol-1-yl)pyridin-2-yl)morpholine | 374 (b) | 141 | * |
| 51 | 3-ethyl-7-(4-(6-(1-methyl-1H-pyrazol-4-yl)-1H-indazol-1-yl)pyridin-2-yl)-5,6,7,8-tetrahydro-[1,2,4]triazolo[4,3-a]pyrazine | 425 (b) | 217 | * |
| 52 | 7-(4-(6-(1-methyl-1H-pyrazol-4-yl)-1H-indazol-1-yl)pyridin-2-yl)-5,6,7,8-tetrahydroimidazo[1,2-a]pyrazine | 396 (b) | 189 | * |
| 53 | 3-methyl-1-(4-(6-(1-methyl-1H-pyrazol-4-yl)-1H-indazol-1-yl)pyridin-2-yl)pyrrolidin-3-ol | 374 (b) | 131 | * |

| Ex | Structure | LCMS m/z (method) | LRRK2 IC$_{50}$ (nM) | Rat AUC 10 mpk PO (μM · h) |
|---|---|---|---|---|
| 54 | 6-(1-methyl-1H-pyrazol-4-yl)-1-(2-(4-(pyrimidin-4-yl)piperazin-1-yl)pyridin-4-yl)-1H-indazole | 437 (b) | 97 | * |
| 55 | 2-(4-(4-(6-(1-methyl-1H-pyrazol-4-yl)-1H-indazol-1-yl)pyridin-2-yl)piperazin-1-yl)ethanol | 403 (b) | 70 | * |
| 56 | This space intentionally left blank | * | * | * |
| 57 | This space intentionally left blank | * | * | * |
| 58 | This space intentionally left blank | * | * | * |
| 59 | This space intentionally left blank | * | * | * |
| 60 | This space intentionally left blank | * | * | * |
| 61 | This space intentionally left blank | * | * | * |

Scheme 12

The Preparation of Example 62

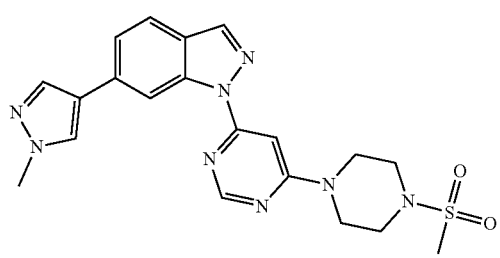 [SMILES: Cn1cc(-c2ccc3cnn(-c4cc(N5CCN(S(C)(=O)=O)CC5)ncn4)c3c2)cn1]

Step 1:

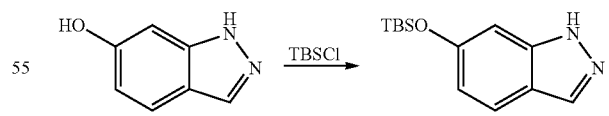

With ice/water bath cooling, to a solution of compound 6-hydroxyindazole (5.0 g, 37.3 mmol) and imidazole (4.1 g, 60.3 mmol) in DMF (30 mL) was added TBSCl (3.6 g, 37.3 mmol) over a period of 30 min. The reaction was stirred overnight. Water (25 mL) was added slowly and the resulting mixture was extracted with EA (3×25 mL). The combined organic layers were washed with water (2×25 mL), and brine (25 mL), dried over Na$_2$SO$_4$, filtered, and evaporated to give a red oil, which was further purified by flash chromatography (elute: PE/EA=6/1-2/1) to afford the desired compound. MS (ESI) m/z=249.3 [M+1]+.

Step 2:

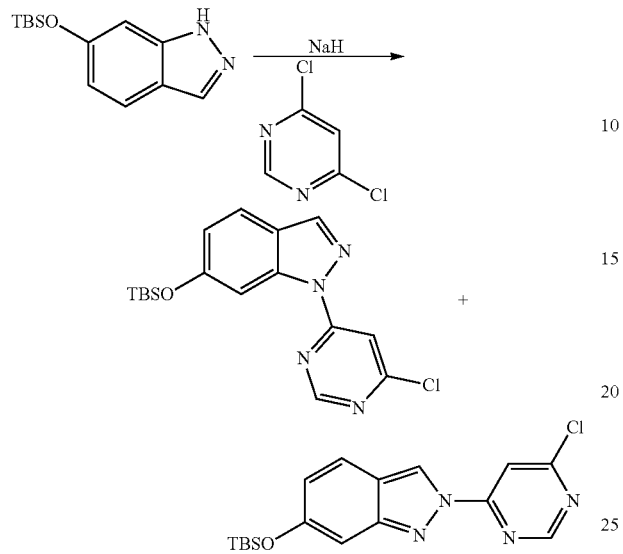

With ice/water bath cooling, to a solution of the product from Step 1 (3.0 g, 12 mmol), and 4,6-dichloropyrimidine (2.5 g 16.8 mmol) in THF (30 mL), NaH (60%, 900 mg, 22.5 mmol) was added portionwise. The reaction was stirred at 40° C. for 3 h. Water (25 mL) was added to the reaction slowly and the resulted mixture was extracted with EA (3×25 mL). The combined organic layers were washed with water (2×25 mL), and brine (25 mL), dried over Na$_2$SO$_4$, filtered, and evaporated to give a yellow oil, which was further purified by flash chromatography (elute: PE/EA=100/1-30/1) to afford the desired product and its regioisomer. MS (ESI) m/z=361.2 [M+1]+.

Step 3:

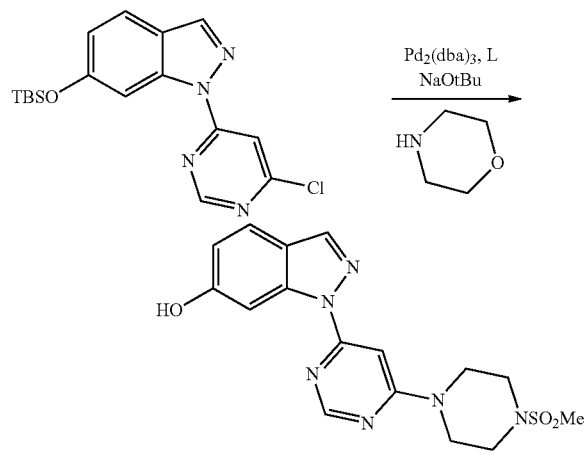

The product from Step 2 (3 g, 8.33 mmol), NaO$^t$Bu (2.41.2 g, 25 mmol), Pd$_2$(dba)$_3$ (3 g, 3.28 mmol) and morpholine (1.5 g, 17.2 mmol), 1,4-bis(2,6-diisoproplphenyl)-3,4-dihydro-2H-pyrrolium chloride (1.4 g, 3.29 mmol) were mixed in DMF (100 mL). The reaction mixture was heated in an oil bath at 120° C. for 8 h. The mixture was cooled to room temperature. Water (500 mL) was added to the reaction and the resulting mixture was extracted with EA (3×200 mL). The extracts were combined and washed with water (2×200 mL) and brine (200 mL), dried over Na$_2$SO$_4$, filtered, and evaporated to give a brown oil, which was further purified by flash chromatography (elute: DCM/MeOH=10/1) to give the desired product. MS (ESI) m/z=374.1 [M+1]+.

Step 4:

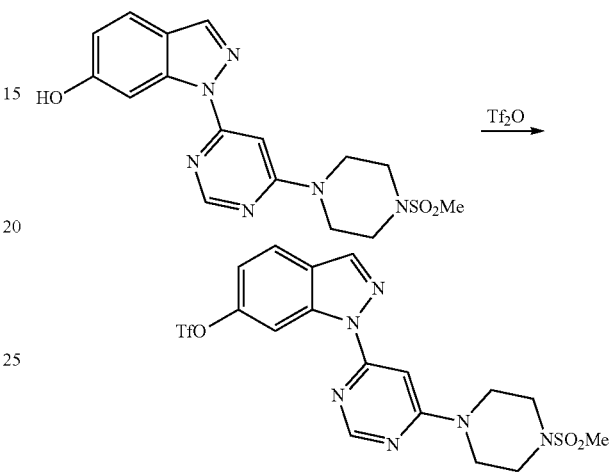

With ice/water bath cooling, to a solution of the product from Step 3 (0.30 g, 0.80 mmol) and pyridine (0.278 g, 3.5 mmol) in THF (2 mL) was added Tf$_2$O (0.6 g, 2.13 mmol) dropwise. The reaction was stirred at 0° C. for 15 min and at room temperature for 45 min. The resulted mixture was purified with Pre-TLC plate (elute: PE/EA=2/1) to give the desired product. MS (ESI) m/z=507.1 [M+1]+.

Step 5:

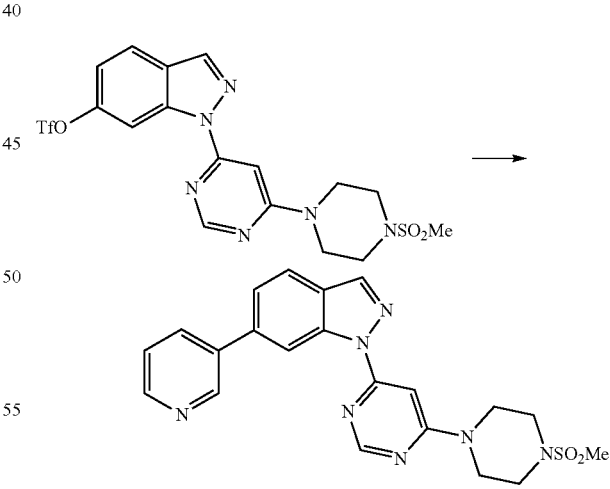

The product from Step 4 (50 mg, 0.1 mmol), pyridin-3-ylboronic acid (25 mg, 0.2 mmol), Na$_2$CO$_3$ (30 mg, 0.28 mmol) and Pd(dppf)Cl$_2$ (8 mg, 0.01 mmol) were taken up into a mixed solvent of toluene/EtOH/H$_2$O (1 mL/0.5 mL/0.5 mL). After being degassed and recharged with argon, the reaction was heated at 70° C. overnight and then filtered. The filtrate was evaporated and the residual was purified with Pre-TLC plate (elute: PE/EA=1/1) to give 1-{6-[4-(methylsulfonyl)piperazin-1-yl]pyrimidin-4-yl}-6-pyridin-3-yl-1H-indazole (Example 62). MS (ESI) m/z=436.2 [M+1]$^+$; LRRK2 IC$_{50}$: 486 nM.

| Ex | Structure | LCMS m/z (method) | LRRK2 IC$_{50}$ (nM) | Rat AUC 10 mpk PO (μM · h) |
|----|-----------|-------------------|----------------------|-----------------------------|
| | IUPAC Name | | | |
| 62 | 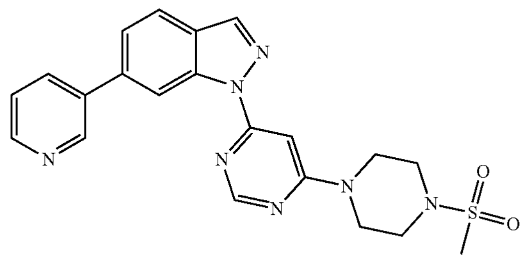 [SMILES: CS(=O)(=O)N1CCN(c2cc(-n3ncc4ccc(-c5cccnc5)cc43)ncn2)CC1] | 436.2 (c) | 486 | * |
| | 1-{6-[4-(methylsulfonyl)piperazin-1-yl]pyrimidin-4-yl}-6-pyridin-3-yl-1H-indazole | | | |

TABLE 12.1

Utilizing the requisite boronic acid and a method similar to that outlined in Scheme 12, the following Examples were prepared:

| Ex | Structure | LCMS m/z (method) | LRRK2 IC$_{50}$ (nM) | Rat AUC 10 mpk PO (μM · h) |
|----|-----------|-------------------|----------------------|-----------------------------|
| | IUPAC Name | | | |
| 63 | 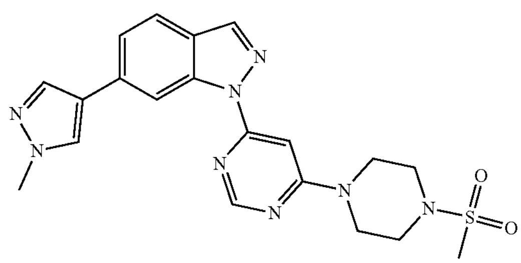 [SMILES: Cn1cc(-c2ccc3cnn(-c4cc(N5CCN(S(C)(=O)=O)CC5)ncn4)c3c2)cn1] | 439.1 (c) | 317 | * |
| | 6-(1-methyl-1H-pyrazol-4-yl)-1-{6-[4-(methylsulfonyl)piperazin-1-yl]pyrimidin-4-yl}-1H-indazole | | | |
| 64 | 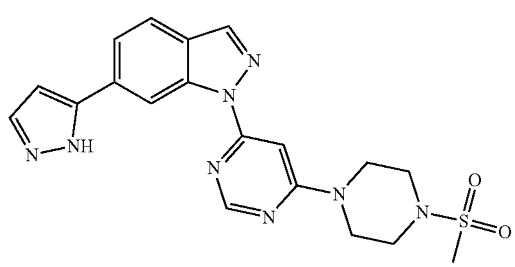 [SMILES: CS(=O)(=O)N1CCN(c2cc(-n3ncc4ccc(-c5ccn[nH]5)cc43)ncn2)CC1] | 425.2 (c) | 18 | * |
| | 1-{6-[4-(methylsulfonyl)piperazin-1-yl]pyrimidin-4-yl}-6-(1H-pyrazol-5-yl)-1H-indazole | | | |
| 65 | This space intentionally left blank | * | * | * |

*

TABLE 12.1-continued

Utilizing the requisite boronic acid and a method similar to that outlined in Scheme 12, the following Examples were prepared:

| Ex | Structure | LCMS m/z (method) | LRRK2 IC$_{50}$ (nM) | Rat AUC 10 mpk PO (μM · h) |
|---|---|---|---|---|
| 66 | 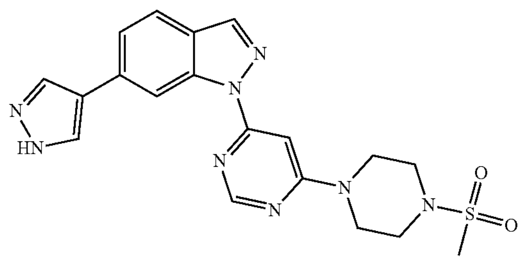 [SMILES: CS(=O)(=O)N1CCN(c2cc(-n3ncc4ccc(-c5cn[nH]c5)cc43)ncn2)CC1] | 425.1 (c) | 68 | * |

1-{6-[4-(methylsulfonyl)piperazin-1-yl]pyrimidin-4-yl}-6-(1H-pyrazol-4-yl)-1H-indazole Scheme 13

The Preparation of Example 67

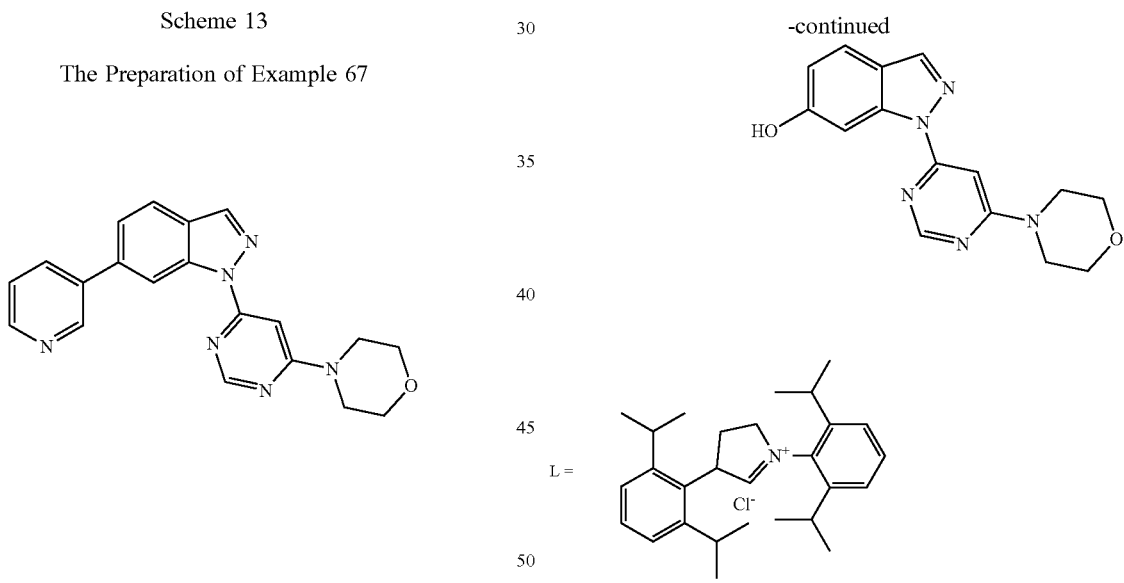

Step 1:

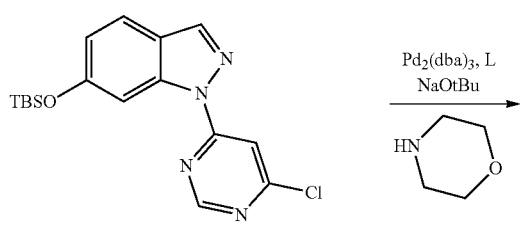

The material prepared in Step 2 of Scheme 12 (1.5 g, 4.17 mmol), NaO$^t$Bu (1.2 g, 12.5 mmol), Pd$_2$(dba)$_3$ (1.5 g, 1.63 mmol) and morpholine (700 mg, 8.04 mmol), 1,4-bis(2,6-diisoproplphenyl)-3,4-dihydro-2H-pyrrolium chloride(697 mg, 1.63 mmol) were mixed in DMF (50 mL). The tube was sealed and then heated in an oil bath at 120° C. for 8 h. The mixture was cooled to room temperature. Water (250 mL) was added to the reaction and the resulting mixture was extracted with EA (3×100 mL). The extracts were combined and washed with water (2×100 mL) and brine (100 mL), dried over Na$_2$SO$_4$, filtered, and evaporated to give a brown oil, which was further purified by flash chromatography (elute: DCM/MeOH=10/1) to give the desired product.

Step 2:

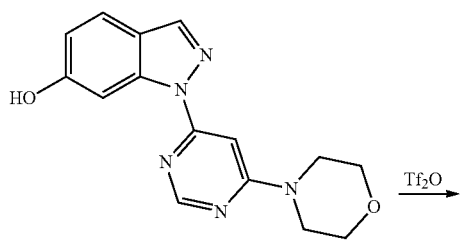

Step 3:

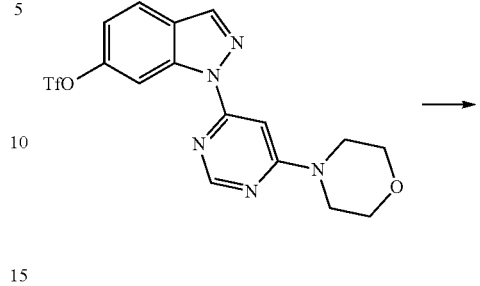

The product from Step 2 (0.9 g, 3.03 mmol) and pyridine (0.95 g, 12.02 mmol) were mixed in THF (8 ml) and the solution was cooled to 0° C. To the above solution was added trifluoromethanesulfonic anhydride (2 g, 7.09 mmol) dropwise and then the reaction was stirred at 0° C. for 15 min and then room temperature for 45 min. The resulting mixture was purified by flash chromatography (elute: DCM/MeOH=10/1) to give the desired product.

The product from Step 2 (0.2 g, 0.47 mmol), pyridin-3-ylboronic acid (0.12 g, 0.98 mmol), Na$_2$CO$_3$ (0.12 g, 1.1 mmol) and Pd(dppf)Cl$_2$ (0.035 g, 0.048 mmol) were taken up into a mixed solvent of toluene/EtOH/H$_2$O (2 mL/1 mL/1 mL). After being degassed and recharged with argon, the reaction was sealed and heated at 70° C. overnight and then cooled to room temperature. The resulting mixture was concentrated in vacuo and the residue was extracted using acetone, filtered and purified using Prep-TLC plate (elute: PE/EA=1/1) to give 1-(6-morpholin-4-ylpyrimidin-4-yl)-6-pyridin-3-yl-1H-indazole (Example 67). MS (ESI) m/z=359.2 [M+1]$^+$; LRRK2 IC$_{50}$: 130 nM.

| Ex | Structure | LCMS m/z (method) | LRRK2 IC$_{50}$ (nM) | Rat AUC 10 mpk PO (μM · h) |
|---|---|---|---|---|
| | IUPAC Name | | | |
| 67 | 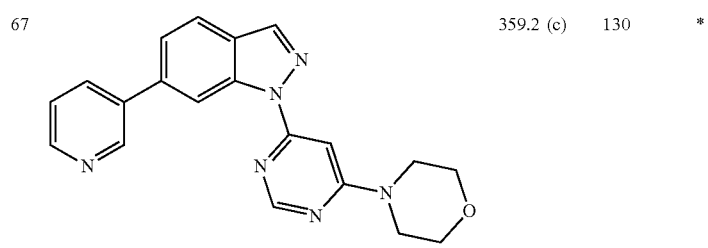 | 359.2 (c) | 130 | * |
| | 1-(6-morpholin-4-ylpyrimidin-4-yl)-6-pyridin-3-yl-1H-indazole | | | |

TABLE 13.1

Utilizing the requisite boronic acid and a method similar to that outlined in Scheme 13, the following Examples were prepared:

| Ex | Structure | LCMS m/z (method) | LRRK2 IC$_{50}$ (nM) | Rat AUC 10 mpk PO (μM · h) |
|----|-----------|-------------------|----------------------|------------------------------|
| | IUPAC Name | | | |
| 68 | 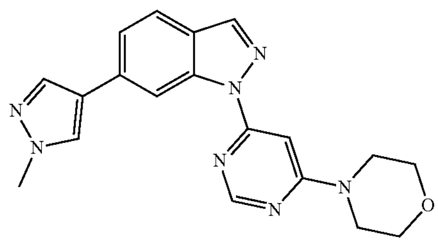 [SMILES: Cn1cc(-c2ccc3cnn(-c4cc(N5CCOCC5)ncn4)c3c2)cn1] | 362.2 (c) | 79 | * |
| | 6-(1-methyl-1H-pyrazol-4-yl)-1-(6-morpholin-4-ylpyrimidin-4-yl)-1H-indazole | | | |
| 69 | 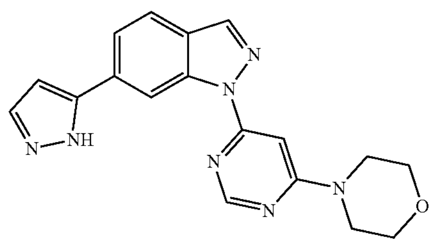 [SMILES: c1cc(-c2ccc3cnn(-c4cc(N5CCOCC5)ncn4)c3c2)[nH]n1] | 348.2 (c) | 10.5 | * |
| | 1-(6-morpholin-4-ylpyrimidin-4-yl)-6-(1H-pyrazol-5-yl)-1H-indazole | | | |
| 70 | 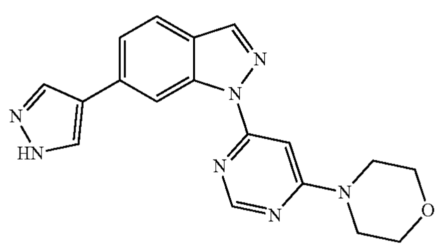 [SMILES: c1nc(N2CCOCC2)cc(-n2ncc3ccc(-c4cn[nH]c4)cc32)n1] | 348.3 (c) | 77 | * |
| | 1-(6-morpholin-4-ylpyrimidin-4-yl)-6-(1H-pyrazo-4-yl)-1H-indazole | | | |
| 71 | 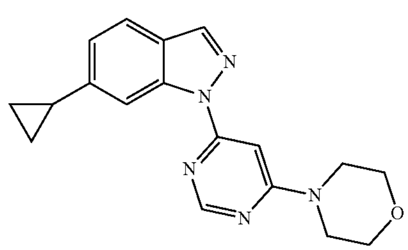 [SMILES: c1nc(N2CCOCC2)cc(-n2ncc3ccc(C4CC4)cc32)n1] | 322.3 (c) | 231 | * |
| | 6-cyclopropyl-1-(6-morpholin-4-ylpyrimidin-4-yl)-1H-indazole | | | |
| 72 | This space intentionally left blank | * (c) * | * | * |

LCMS Conditions

Method a:—

Column Agilent SBC (3.0×50 mm, 1.8 u); Flow 1.0 mL/min; solvent A: H$_2$O-0.1% TFA; solvent B: ACN-0.1% TFA; GRADIENT TABLE: 0 min: 10% B, 0.3 min: 10% B, 1.5 min: 95% B, 2.70 min: 95% B, 2.76 min: 10% B, stop time 3.60 min, PostTime 0.70 min.

Method b:

Waters Acquity UPLC/MS, Electrospray positive ion mode; Column: Waters Acquity UPLC BEH C18, 2.1×50 mm, 1.7 micron; Gradient elution 5:95 to 100:0 MeCN (0.1% NH$_4$OH):water (0.1% NH$_4$OH) over 1.4 min 0.8 mL/min; UV: 220 nm.

Method c:

Mobile Phase: A: water (10 mM NH$_4$HCO$_3$) B: Acetonitrile
Gradient: 5% B for 0.2 min, increase to 95% B within 1.5 min,
95% B for 1.5 min, back to 5% B within 0.01 min.
Flow Rate: 1.8 mL/min
Column: XBridge C18, 4.6*50 mm, 3.5 um
Oven Temperature: 50° C.

Representative Example of a Pharmacokinetic Measurement

The pharmacokinetics of a compound of the invention (amorphous free form) can be studied following single intravenous and/or oral administration to mouse, rat, dog and/or monkey. In the present study, the pharmacokinetics of selected compounds of the invention (amorphous free form) were studied following single intravenous and/or oral administration to rat. The IV solution formulations contained 30% captisol/70% water or 1/1 DMSO/PEG-400. The PO solution formulations contained 10% tween/90% PEG-400 or 40% PEG-400/25% of a aqueous HPBCD solution (20%)/35% water. All IV formulations were given as solutions and all PO doses were given as well-behaved suspensions or solutions. Animals were fasted prior to oral dosing in single-dose studies. Oral bioavailability was estimated using non-cross-over study designs (n=2 or 3). Plasma samples were assayed using protein precipitation with acetonitrile/methanol (90/10, v/v) followed by HPLC/MS/MS analysis employing positive-ion Turbo IonSpray ionization. Plasma concentration-time data were analyzed by non-compartmental methods and expressed as AUC (area under the curve) values. Holding dose constant, higher oral AUC values represent greater oral plasma exposure.

The tables above provide oral AUC values for example 1, 8, 12, 17, and 20, in which the compound was dosed in rats at 10 mpk via a method similar to that described above.

Biological Assays

The data presented for the Km ATP LanthaScreen™ Assay represents mean IC$_{50}$ values based on several test results and may have reasonable deviations depending on the specific conditions and reagents used. Reagents for the LRRK2 Km ATP LanthaScreen™ Assay were purchased from Life Technologies Corporation.

LRRK2 Km ATP LanthaScreen™ Assay a) 400 nl of a 1:2.15 serial dilution of test compound (98 µM top assay concentration) is spotted via Labcyte Echo to certain wells in a 384 well black, untreated plate. Control wells contain 400 nl of either DMSO or 400 nl of a known inhibitor in DMSO.

b) 10 µl of a 2.5 nM LRRK2 (G2019S mutation, GST-LRRK2 (amino acids 970-2527)) enzyme solution in 1× assay buffer (50 mM Tris pH 8.5, 10 mM MgCl$_2$, 0.01% Brij-35, 1 mM EGTA, 2 mM DTT, 0.05 mM NaVO$_4$) is added to all wells.

c) A 30 minute room temperature incubation is followed by addition of 10 µl of 800 nM fluorescein labeled LRRKtide peptide substrate and 186 µM ATP solution in 1× assay buffer to all wells.

d) After a 60 minute room temperature incubation, 20 µl of TR-FRET Dilution Buffer (Invitrogen PV3756B) containing 4 nM Tb-labeled anti-phospho LRRKtide antibody and 20 mM EDTA is added to all wells.

e) Plates are incubated at room temperature for 1 hour and read on an Envision™ multi-mode plate reader with LanthaScreen™ settings. Results are analysed using Assay Data Analyzer.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed:

1. A compound of Formula (I):

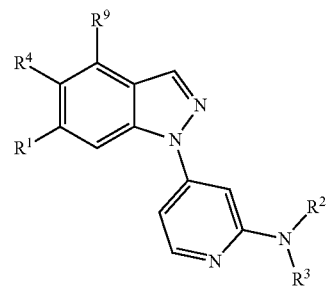

or a pharmaceutically acceptable salt thereof,
wherein R$^1$ is pyrazolyl, wherein said pyrazolyl is optionally substituted with one to three substituents independently selected from the group consisting of:
a) halo,
b) cyano,
c) hydroxyl,
d) oxo,
e) C$_{1-3}$ alkyl, which is optionally substituted with one to four substituents independently selected from the group consisting of hydroxyl, halo, cyano, OC$_{1-3}$ alkyl and NR$^c$R$^d$,
f) OC$_{1-3}$ alkyl, which is optionally substituted with one to four substituents independently selected from the group consisting of hydroxyl, halo, cyano, OC$_{1-3}$ alkyl, NR$^c$R$^d$, and aryl, g) $C_{3-8}$ cycloalkyl, which is optionally substituted with one to four substituents independently selected from the group consisting of hydroxyl, halo, cyano, $OC_{1-3}$ alkyl and $NR^cR^d$,
h) aryl, which is optionally substituted with one to four substituents independently selected from the group consisting of hydroxyl, halo, cyano, $OC_{1-3}$ alkyl, $S(O)_mNR^cR^d$, $C(O)NR^cR^d$ and $NR^cR^d$,
i) heteroaryl, which is optionally substituted with one to four substituents independently selected from the group consisting of hydroxyl, halo, cyano, $OC_{1-3}$ alkyl, $S(O)_mNR^cR^d$, $C(O)NR^cR^d$ and $NR^cR^d$,
j) $C_{4-8}$ cycloalkenyl, which is optionally substituted with one to four substituents independently selected from the group consisting of hydroxyl, halo, cyano, $OC_{1-3}$ alkyl and $NR^cR^d$;

$R^2$ and $R^3$ are taken together with the atoms to which they are shown attached to form a morpholinyl group, a piperazinyl group, a piperidinyl group, an azetidinyl group, or a pyrrolidinyl group, wherein each said group is optionally substituted with from 1 to 4 substituents selected from the group consisting of:
a) halo,
b) oxo,
c) $OR^5$,
d) $NR^cR^d$,
e) $S(O)_mR^5$,
f) $S(O)_mR^7$,
f) $R^5$,
g) $R^6$,
h) $R^7$,
i) $(C{=}O)R^5$,
j) $(C{=}O)OR^5$ and
k) $(C{=}O)R^7$;

$R^4$ is selected from the group consisting of: hydrogen, halo, cyano, $OR^5$, aryl, $C_{3-8}$ cycloalkyl, $C_{4-8}$ cycloalkenyl, and $C_{1-6}$ alkyl, which is optionally substituted with one to three substitutents independently selected from the group consisting of halo, cyano, $OC_{1-3}$ alkyl, $NR^cR^d$ and hydroxy;

$R^5$ is selected from the group consisting of hydrogen or $C_{1-6}$ alkyl, which is optionally substituted with one to three substituents independently selected from the group consisting of:
a) halo,
b) hydroxyl,
c) $OC_{1-6}$ alkyl,
d) $NR^cR^d$,
e) $(C{=}O)NR^cR^d$,
f) $S(O)_mR^8$,
g) $S(O)_mR^7$,
h) $R^7$, and
i) $OR^7$;

$R^6$ is $C_{1-6}$ alkyl, which is optionally substituted with one to three substituents independently selected from the group consisting of halo and hydroxyl;

or $R^5$ and $R^6$ can be taken together with the atoms to which they are attached to form a 3 to 8 membered carbocyclic, aryl wherein said carbocyclic, and aryl are optionally substituted with one to three substituents independently selected from the group consisting of:
a) halo,
b) oxo,
c) cyano,
d) hydroxyl, e) $C_{1-3}$ alkyl, which is optionally substituted with one to three halo,
f) $C_{3-8}$ cycloalkyl,
g) $OC_{1-3}$ alkyl, which is optionally substituted with one to three halo, and
h) $OC_{3-8}$ cycloalkyl;

$R^7$ is selected from the group consisting of $C_{3-8}$ cycloalkyl, $C_{4-8}$ cycloalkenyl, and aryl, wherein said cycloalkyl, cycloalkenyl, and aryl groups are optionally substituted with one to three substituents independently selected from the group consisting of:
a) halo,
b) cyano,
c) hydroxyl,
d) oxo,
e) $C_{1-3}$ alkyl, which is optionally substituted with one to four substituents independently selected from the group consisting of hydroxyl, halo, cyano, $OC_{1-3}$ alkyl and $NR^cR^d$,
f) $OC_{1-3}$ alkyl, which is optionally substituted with one to four substituents independently selected from the group consisting of hydroxyl, halo, cyano, $OC_{1-3}$ alkyl, $NR^cR^d$, aryl and heteroaryl,
g) $C_{3-8}$ cycloalkyl, which is optionally substituted with one to four substituents independently selected from the group consisting of hydroxyl, halo, cyano, $OC_{1-3}$ alkyl and $NR^cR^d$,
h) aryl, which is optionally substituted with one to four substituents independently selected from the group consisting of hydroxyl, halo, cyano, $OC_{1-3}$ alkyl, $S(O)_mNR^cR^d$, $C(O)NR^cR^d$ and $NR^cR^d$,
i) $C_{4-8}$ cycloalkenyl, which is optionally substituted with one to four substituents independently selected from the group consisting of hydroxyl, halo, cyano, $OC_{1-3}$ alkyl and $NR^cR^d$;

$R^8$ is hydrogen or $C_{1-6}$ alkyl, which is optionally substituted with one to three substituents independently selected from the group consisting of:
a) halo,
b) cyano,
c) hydroxyl,
d) $OC_{1-3}$ alkyl, which is optionally substituted with one to four substituents independently selected from the group consisting of hydroxyl, halo and $NR^eR^f$, and
e) $C_{3-8}$ cycloalkyl;

$R^9$ is selected from the group consisting of:
a) $C_{1-3}$ alkyl, which is optionally substituted with one to three substituents independently selected from the group consisting of halo,
b) halo,
c) cyano,
d) hydroxyl, and
e) $OC_{1-3}$ alkyl, which is optionally substituted with one to three substituents independently selected from the group consisting of halo;

$R^a$ is selected from the group consisting of hydrogen and $C_{1-6}$ alkyl;
$R^b$ is selected from the group consisting of hydrogen and $C_{1-6}$ alkyl;
$R^C$ is selected from the group consisting of:
a) hydrogen,
b) $C_{1-3}$ alkyl, which is optionally substituted with one to three substituents independently selected from the group consisting of halo, hydroxyl, cyano, aryl, $NH(C_{1-3}$ alkyl), $N(C_{1-3}$ alkyl)$_2$, $OC_{1-6}$ alkyl, and $C_{3-8}$ cycloalkyl;

$R^d$ is selected from the group consisting of:
a) hydrogen,
b) $C_{3-8}$ cycloalkyl,
c) $C_{1-3}$ alkyl,
d) (C=O)$C_{1-3}$ alkyl,
e) aryl, and
wherein said cycloalkyl, alkyl, and aryl groups are each optionally substituted with one to three substituents independently selected from the group consisting of halo, hydroxyl, cyano, $R^8$, $SO_2R^8$, $OC_{1-6}$ alkyl and $C_{3-8}$ cycloalkyl;
$R^e$ is selected from the group consisting of hydrogen and $C_{1-3}$ alkyl;
$R^f$ is selected from the group consisting of hydrogen and $C_{1-3}$ alkyl; and
m is an integer from zero to two.

2. The compound of claim 1, or a pharmaceutically acceptable salt thereof, wherein $R^4$ is H and $R^9$ is selected from the group consisting of H and halo.

3. The compound of claim 2 wherein $R^1$ is pyrazolyl, wherein said pyrazolyl is optionally substituted with one to three substituents independently selected from the group consisting of: alkyl, alkoxy, halo, cyano, hydroxyl, and oxo.

4. A compound, or a pharmaceutically acceptable salt thereof, said compound selected from the group consisting of:

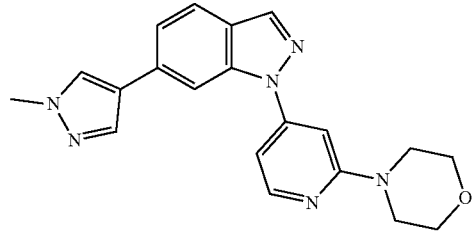

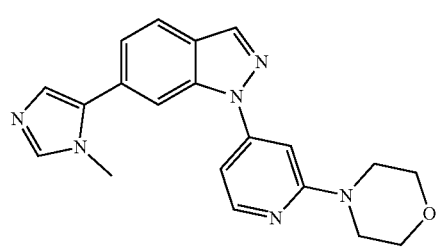

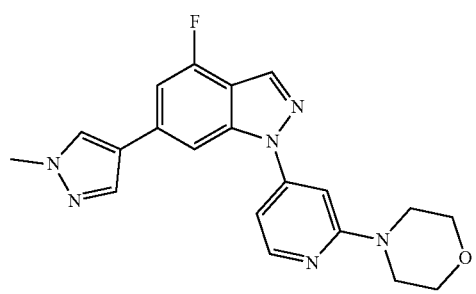

-continued

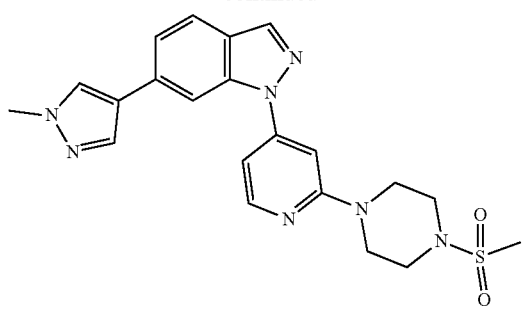

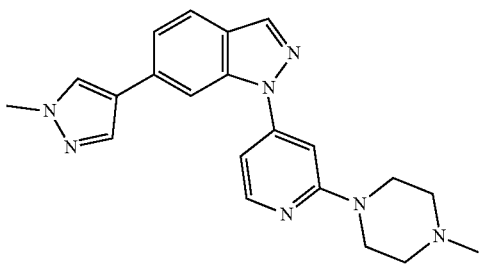

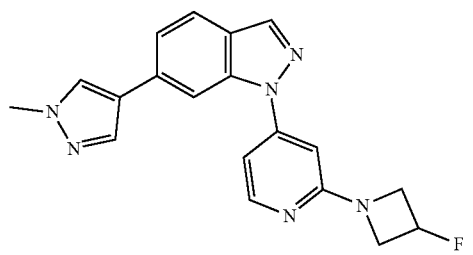

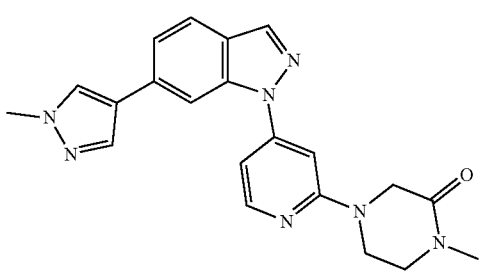

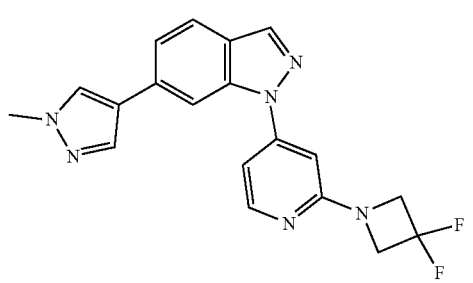

-continued
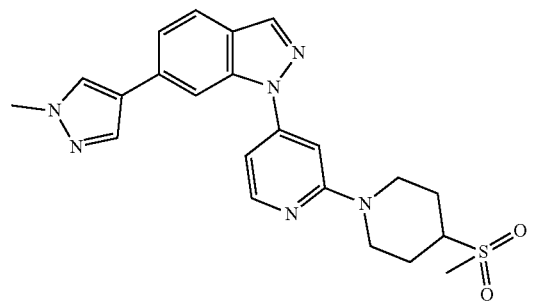
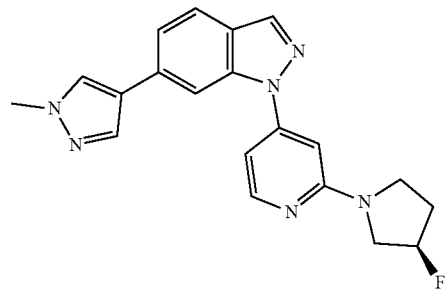
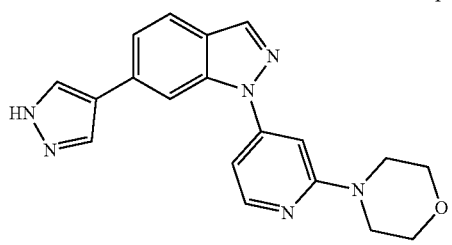
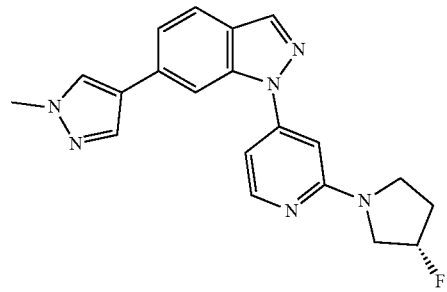
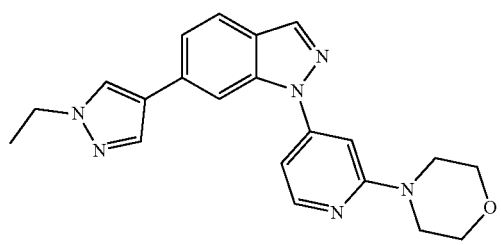
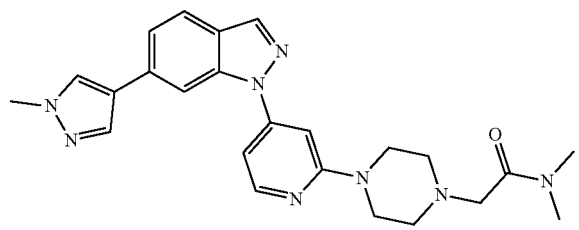
-continued
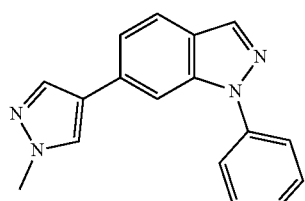
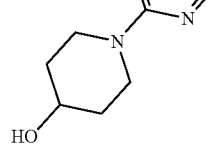
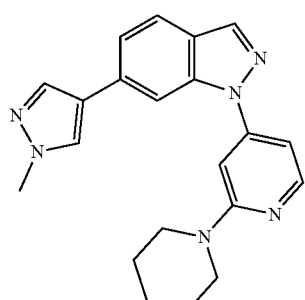
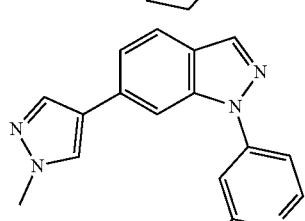
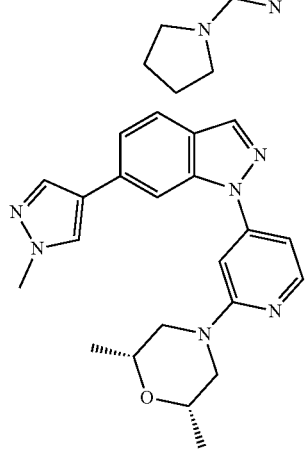
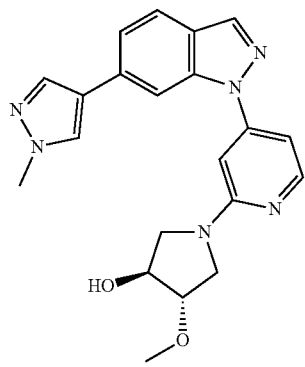

-continued
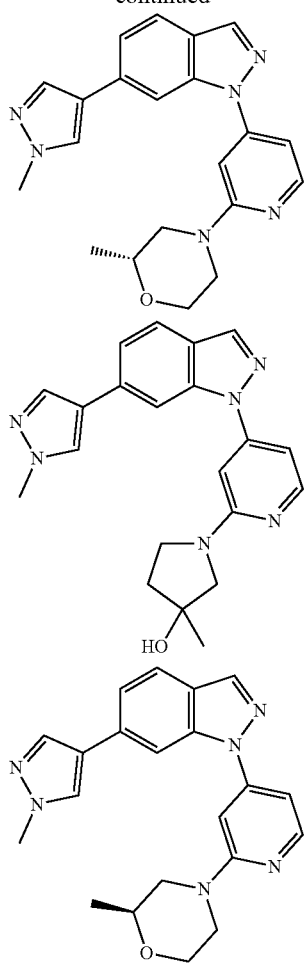
-continued
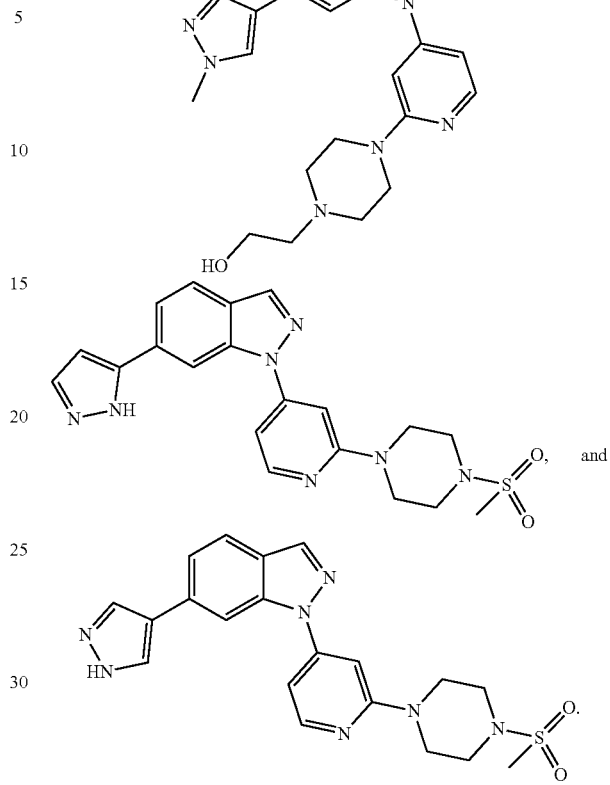
5. A pharmaceutical composition comprising a compound of claim 1, and a pharmaceutically acceptable carrier.
* * * * *